US009821076B2

(12) United States Patent
Acharjee

(10) Patent No.: US 9,821,076 B2
(45) Date of Patent: Nov. 21, 2017

(54) CHIMERIC VSV-G PROTEINS AS NUCLEIC ACID TRANSFER VEHICLES

(71) Applicant: Sujata Acharjee, New York, NY (US)

(72) Inventor: Sujata Acharjee, New York, NY (US)

(73) Assignee: Serendipity Biotech Inc., New York, NY (US)

( * ) Notice: Subject to any disclaimer, the term of this patent is extended or adjusted under 35 U.S.C. 154(b) by 91 days.

(21) Appl. No.: 14/695,265

(22) Filed: Apr. 24, 2015

(65) Prior Publication Data

US 2015/0306248 A1    Oct. 29, 2015

Related U.S. Application Data

(60) Provisional application No. 61/984,290, filed on Apr. 25, 2014.

(51) Int. Cl.
| | |
|---|---|
| *A61K 48/00* | (2006.01) |
| *C07K 14/005* | (2006.01) |
| *C07K 14/435* | (2006.01) |
| *C12N 9/22* | (2006.01) |
| *C07K 14/47* | (2006.01) |

(52) U.S. Cl.
CPC ........ *A61K 48/0008* (2013.01); *C07K 14/005* (2013.01); *C07K 14/435* (2013.01); *C07K 14/4722* (2013.01); *C12N 9/22* (2013.01); *C07K 2319/01* (2013.01); *C07K 2319/80* (2013.01); *C07K 2319/85* (2013.01)

(58) Field of Classification Search
None
See application file for complete search history.

(56) References Cited

U.S. PATENT DOCUMENTS

| | | |
|---|---|---|
| 2003/0211590 A1 | 11/2003 | Hwu |
| 2006/0078542 A1 | 4/2006 | Mah et al. |
| 2009/0041724 A1 | 2/2009 | Jensen |
| 2012/0322147 A1 | 12/2012 | Mangeot et al. |

OTHER PUBLICATIONS

Sonnemann KJ, Heun-Johnson H, Turner AJ, Baltgalvis KA, Lowe DA, Ervasti JM. Functional substitution by TAT-utrophin in dystrophin-deficient mice. PLoS Med. 2009.
Ahn, Andrew H.; Kunkel, Louis M.; Syntrophin binds to an alternatively spliced exon of dystrophin. The Journal of Cell Biology 1995;128(3):363-371.
Amenta AR, Yilmaz A, Bogdanovich S, et al. Biglycan recruits utrophin to the sarcolemma and counters dystrophic pathology in mdx mice. Proceedings of the National Academy of Sciences of the United States of America. 2011;108(2):762-767.
Weisbart, Richard H. et al.; An intracellular delivery vehicle for protein transduction of micro-dystrophin. Journal of Drug Targeting. vol. 13, Iss. 2, 2005, 81-87.
Bies RD, Phelps SF, Cortez MD, Roberts R, Caskey CT, Chamberlain JS. Human and murine dystrophin mRNA transcripts are differentially expressed during skeletal muscle, heart, and brain development. Nucleic Acids Research. 1992;20(7):1725-1731.
Blau HM, Webster C, Pavlath GK. Defective myoblasts identified in Duchenne muscular dystrophy. Proceedings of the National Academy of Sciences of the United States of America. 1983;80(15):4856-4860.
Briggs D, Morgan JE. Recent progress in satellite cell/myoblast engraftment—relevance for therapy. The Febs Journal 2013;280(17):4281-4293.
Crosbie, Rachelle H. Sarcospan, the 25-kDa Transmembrane Component of the Dystrophin-Glycoprotein Complex. J. Biol. Chem. 1997 272: 31221-31224.
Danialou, Gawiyou. Dystrophin-deficient cardiomyocytes are abnormally vulnerable to mechanical stress-induced contractile failure and injury. FASEB J Jul. 2001 15:1655-1657; published ahead of print May 29, 2001.
Darras BT, Miller DT, Urion DK. Dystrophinopathies. Sep. 5, 2000 [Updated Nov. 26, 2014]. In: Pagon RA, Adam MP, Ardinger HH, et al., editors. GeneReviews® [Internet]. Seattle (WA): University of Washington, Seattle; 1993-2015. Available from: http://www.ncbi.nlm.nih.gov/books/NBK1119/.
Delfin DA, Zang KE, Schill KE, et al. Cardiomyopathy in the dystrophin/utrophin-deficient mouse model of severe muscular dystrophy is characterized by dysregulation of matrix metalloproteinases. Neuromuscular disorders: NMD. 2012;22(11):1006-1014. doi:10.1016/j.nmd.2012.05.002.
De Luca A. Pre-clinical drug tests in the mdx mouse as a model of dystrophinopathies: an overview. Acta Myologica. 2012;31(1):40-47.
Den Dunnen JT, Grootscholten PM, Bakker E, et al. Topography of the Duchenne muscular dystrophy (DMD) gene: FIGE and cDNA analysis of 194 cases reveals 115 deletions and 13 duplications. American Journal of Human Genetics. 1989;45(6):835-847.
"Dystrophin protein—Protein—NCBI", http://www.ncbi.nlm.nih.gov/protein/Q14205, printed May 28, 2015.
Epstein, Wallace V. Treatment of Rheumatoid Arthritis with a Tumor Necrosis Factor Receptor-Fc Fusion Protein. The New England Journal of Medicine. 337(21):1559-1560.
Vessillier, Sandrine et al. Latent cytokines: development of novel cleavage sites and kinetic analysis of their differential sensitivity to MMP-1 and MMP-3. Protein Engineering, Design and Selection (2004) 17 (12): 829-835.
Chen X, Zaro J, Shen W-C. Fusion Protein Linkers: Property, Design and Functionality. Advanced drug delivery reviews. 2013;65(10):1357-1369.
Kanda, Teru et al. Histone-GFP fusion protein enables sensitive analysis of chromosome dynamics in living mammalian cells. Current Biology, vol. 8, Issue 7, 377-385.Kanda, Teru et al. Histone-GFP fusion protein enables sensitive analysis of chromosome dynamics in living mammalian cells. Current Biology, vol. 8, Issue 7, 377-385.

(Continued)

*Primary Examiner* — Suzanne M Noakes
(74) *Attorney, Agent, or Firm* — Wiggin and Dana LLP; Gregory S. Rosenblatt; Andrew D. Bochner

(57) ABSTRACT

The design and generation of a number of chimeric VSV-G (or VSV-G variants) proteins are used as transfer vehicles to enhance delivery of nucleic acids like plasmid DNA, single and double stranded DNA and RNA, and antisense oligonucleotides into human and animal cells. These chimeric VSV-G protein-nucleic acid transfer vehicles have widespread applications to deliver nucleic acids for exon skipping and gene delivery for gene replacement in human and animals.

16 Claims, 6 Drawing Sheets

(56) References Cited

OTHER PUBLICATIONS

Vesicular stomatitis Indiana virus, http://www.uniprot.org/uniprot/P04884.txt?version=71, printed May 28, 2015.
Invitation to Pay Additional Fees from International Patent Application No. PCT/US2015/027496 dated Aug. 13, 2015.
International Search Report and Written Opinion from International Patent Application No. PCT/US2015/018263, dated Sep. 14, 2015.
Gallione, C.J. and Rose, J.K. 'A single amino acid substitution in a hydrophobic domain causes temperature-sensitive cell-surface transport of a mutant viral glycoprotein' J. Virol. 54 (2), 374-382 (1985) OWT mRNA sequence.
EMBL Accession No. AY400521 '*Homo sapiens* HIST1H2AE gene, Virtual Transcript, partial sequence, genomic survey sequence' Oct. 2, 2013. DNA sequence.
International Search Report and Written Opinion from International Patent Application No. PCT/US2015/027496, dated Nov. 6, 2015.

providing a therapeutic compound comprising a chimeric protein including VSV-G, a nucleic acid binding protein, and at least one nucleic acid — 500 administering to the subject a pharmaceutically active amount of the therapeutic compound — 510

FIG. 5

SEQUENCE LISTING

```
<160> NUMBER OF SEQ ID NOS: 26

<210> SEQ ID NO 1
<211> LENGTH: 1923
<212> TYPE: DNA
<213> ORGANISM: Artificial Sequence
<220> FEATURE:
<223> OTHER INFORMATION: H2A VSV-G Chimeric Protein Nucleotide Sequence
<220> FEATURE:
<221> NAME/KEY: misc_feature
<222> LOCATION: (1)..(1923)

<400> SEQUENCE: 1
atgtctggac gtggaaagca aggcggcaaa gctcgggcaa aagctaaaac gcgttcttcc      60
agggccggtc ttcagtttcc agttggccgt gtgcaccgcc tcctccgcaa aggcaactac     120
tccgaacgag tcggggccgg cgctccagtg tacctggcag cggtgctgga atatctgacg     180
gccgagatct tagagctagc tggcaacgcg gctcgcgaca ataagaagac ccgcatcatc     240
ccgcgccacc tgcagctagc catccgcaac gacgaggagc taaataagct tctaggtcgc     300
gtgaccatcg cgcagggcgg tgtcctgccc aacatccagg ccgtattgct gcctaagaag     360
acggagagcc accataaggc caagggcaag aagtgccttt tgtacttagc ttttttattc     420
atcggggtga attgcaagtt caccatagtt tttccacaca accaaaaagg aaactggaaa     480
aatgttcctt ccaattacca ttattgcccg tcaagctcag atttaaattg gcataatgac     540
ttaataggca cagccttaca agtcaaaatg cccaagagtc acaaggctat tcaagcagac     600
ggttggatgt gtcatgcttc caaatgggtc actacttgtg atttccgctg gtacggaccg     660
aagtatataa cacattccat ccgatccttc actccatctg tagaacaatg caaggaaagc     720
attgaacaaa cgaaacaagg aacttggctg aatccaggct tccctcctca aagttgtgga     780
tatgcaactg tgacggatgc tgaagcagcg attgtccagg tgactcctca ccatgtgctt     840
gttgatgaat acacaggaga atgggttgat tcacagttca tcaacggaaa atgcagcaat     900
gacatatgcc ccactgtcca taactccaca acctggcatt ccgactataa ggtcaaaggg     960
ctatgtgatt ctaacctcat ttccacggac atcaccttct tctcagagga cggagagcta    1020
tcatccctag gaaaggaggg cacagggttc agaagtaact actttgctta tgaaactgga    1080
gacaaggcct gcaaaatgca gtactgcaag cattggggag tcagactccc atcaggtgtc    1140
tggttcgaga tggctgataa ggatctcttt gctgcagcca gattccctga atgcccagaa    1200
gggtcaagta tctctgctcc atctcagacc tcagtggatg taagtctcat tcaggacgtt    1260
gagaggatct tggattattc cctctgccaa gaaacctgga gcaaaatcag agcgggtctt    1320
```

-continued

```
cccatctctc cagtggatct cagctatctt gctcctaaaa acccaggaac cggtcctgtc    1380
tttaccataa tcaatggtac cctaaaatac tttgagacca gatacatcag agtcgatatt    1440
gctgctccaa tcctctcaag aatggtcgga atgatcagtg aactaccac agaaagggaa     1500 ctgtgggatg actgggctcc atatgaagac gtggaaattg acccaatgg agttctgagg     1560 accagtttag gatataagtt tcctttatat atgattggac atggtatgtt ggactccgat    1620
cttcatctta gctcaaaggc tcaggtgttt gaacatcctc acattcaaga cgctgcttcg    1680
cagcttcctg atgatgagac tttattttt ggtgatactg ggctatccaa aaatccaatc     1740
gagtttgtag aaggttggtt cagtagtggg aagagctcta ttgcctcttt tttctttatc    1800 ataggttaa tcattggact attcttggtt ctccgagttg gtatttatct ttgcattaaa     1860
ttaaagcaca ccaagaaaag acagatttat acagacatag agatgaaccg acttggaaag    1920
taa                                                                  1923
```

```
<210> SEQ ID NO 2
<211> LENGTH: 640
<212> TYPE: PRT
<213> ORGANISM: Artificial Sequence
<220> FEATURE:
<223> OTHER INFORMATION: H2A VSV-G Chimeric Protein Amino Acid Sequence
<220> FEATURE:
<221> NAME/KEY: CHAIN
<222> LOCATION: (1)..(640)

<400> SEQUENCE: 2
```

```
Met Ser Gly Arg Gly Lys Gln Gly Gly Lys Ala Arg Ala Lys Ala Lys
1               5                   10                  15

Thr Arg Ser Ser Arg Ala Gly Leu Gln Phe Pro Val Gly Arg Val His
            20                  25                  30

Arg Leu Leu Arg Lys Gly Asn Tyr Ser Glu Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                85                  90                  95

Leu Leu Gly Arg Val Thr Ile Ala Gln Gly Gly Val Leu Pro Asn Ile
            100                 105                 110

Gln Ala Val Leu Leu Pro Lys Lys Thr Glu Ser His His Lys Ala Lys
        115                 120                 125

Gly Lys Lys Cys Leu Leu Tyr Leu Ala Phe Leu Phe Ile Gly Val Asn
    130                 135                 140

Cys Lys Phe Thr Ile Val Phe Pro His Asn Gln Lys Gly Asn Trp Lys
145                 150                 155                 160

Asn Val Pro Ser Asn Tyr His Tyr Cys Pro Ser Ser Asp Leu Asn
                165                 170                 175

Trp His Asn Asp Leu Ile Gly Thr Ala Leu Gln Val Lys Met Pro Lys
            180                 185                 190

Ser His Lys Ala Ile Gln Ala Asp Gly Trp Met Cys His Ala Ser Lys
        195                 200                 205

Trp Val Thr Thr Cys Asp Phe Arg Trp Tyr Gly Pro Lys Tyr Ile Thr
    210                 215                 220

His Ser Ile Arg Ser Phe Thr Pro Ser Val Glu Gln Cys Lys Glu Ser
```

-continued

Ile Glu Gln Thr Lys Gln Gly Thr Trp Leu Asn Pro Gly Phe Pro Pro
225                 230                 235                 240

Gln Ser Cys Gly Tyr Ala Thr Val Thr Asp Ala Glu Ala Ala Ile Val
            245                 250                 255

Gln Val Thr Pro His His Val Leu Val Asp Glu Tyr Thr Gly Glu Trp
        260                 265                 270

Val Asp Ser Gln Phe Ile Asn Gly Lys Cys Ser Asn Asp Ile Cys Pro
    290                 295                 300

Thr Val His Asn Ser Thr Thr Trp His Ser Asp Tyr Lys Val Lys Gly
305                 310                 315                 320

Leu Cys Asp Ser Asn Leu Ile Ser Thr Asp Ile Thr Phe Phe Ser Glu
            325                 330                 335

Asp Gly Glu Leu Ser Ser Leu Gly Lys Glu Gly Thr Gly Phe Arg Ser
        340                 345                 350

Asn Tyr Phe Ala Tyr Glu Thr Gly Asp Lys Ala Cys Lys Met Gln Tyr
    355                 360                 365

Cys Lys His Trp Gly Val Arg Leu Pro Ser Gly Val Trp Phe Glu Met
370                 375                 380

Ala Asp Lys Asp Leu Phe Ala Ala Arg Phe Pro Glu Cys Pro Glu
385                 390                 395                 400

Gly Ser Ser Ile Ser Ala Pro Ser Gln Thr Ser Val Asp Val Ser Leu
            405                 410                 415

Ile Gln Asp Val Glu Arg Ile Leu Asp Tyr Ser Leu Cys Gln Glu Thr
        420                 425                 430

Trp Ser Lys Ile Arg Ala Gly Leu Pro Ile Ser Pro Val Asp Leu Ser
    435                 440                 445

Tyr Leu Ala Pro Lys Asn Pro Gly Thr Gly Pro Val Phe Thr Ile Ile
450                 455                 460

Asn Gly Thr Leu Lys Tyr Phe Glu Thr Arg Tyr Ile Arg Val Asp Ile
465                 470                 475                 480

Ala Ala Pro Ile Leu Ser Arg Met Val Gly Met Ile Ser Gly Thr Thr
            485                 490                 495

Thr Glu Arg Glu Leu Trp Asp Asp Trp Ala Pro Tyr Glu Asp Val Glu
        500                 505                 510

Ile Gly Pro Asn Gly Val Leu Arg Thr Ser Leu Gly Tyr Lys Phe Pro
    515                 520                 525

Leu Tyr Met Ile Gly His Gly Met Leu Asp Ser Asp Leu His Leu Ser
530                 535                 540

Ser Lys Ala Gln Val Phe Glu His Pro His Ile Gln Asp Ala Ala Ser
545                 550                 555                 560

Gln Leu Pro Asp Asp Glu Thr Leu Phe Phe Gly Asp Thr Gly Leu Ser
            565                 570                 575

Lys Asn Pro Ile Glu Phe Val Glu Gly Trp Phe Ser Ser Trp Lys Ser
        580                 585                 590

Ser Ile Ala Ser Phe Phe Ile Ile Gly Leu Ile Ile Gly Leu Phe
    595                 600                 605

Leu Val Leu Arg Val Gly Ile Tyr Leu Cys Ile Lys Leu Lys His Thr
610                 615                 620

Lys Lys Arg Gln Ile Tyr Thr Asp Ile Glu Met Asn Arg Leu Gly Lys
625                 630                 635                 640

<210> SEQ ID NO 3

<211> LENGTH: 1911
<212> TYPE: DNA
<213> ORGANISM: Artificial Sequence
<220> FEATURE:
<223> OTHER INFORMATION: H2B VSV-G Chimeric Protein Nucleotide Sequence
<220> FEATURE:
<221> NAME/KEY: misc_feature
<222> LOCATION: (1)..(1911)

<400> SEQUENCE: 3

| | | | | | |
|---|---|---|---|---|---|
| atgccagacc | cgtccaaatc | ggctcctgcg | cccaagaagg | gttctaaaaa | ggctgtcacc | 60 |
| aaggcacaga | agaaggacgg | caagaagcgc | aagcgcggcc | gcaaggagag | ctattctatc | 120 |
| tacgtgtaca | aggtgctgaa | gcaggtgcac | cccgacaccg | gcatctcgtc | caaggccatg | 180 |
| ggcatcatga | actccttcgt | caatgacatc | ttcgagcgca | tcgccagcga | ggcctcccgc | 240 |
| ctggcacact | acaacaagcg | ctccaccatc | acgtcccgcg | aagtgcagac | ggccgttcgc | 300 |
| ctgctgctgc | ccggcgagct | ggccaagcac | gccgtgtccg | agggcaccaa | ggctgtcacc | 360 |
| aagtacacca | gctccaagaa | gtgccttttg | tacttagctt | ttttattcat | cggggtgaat | 420 |
| tgcaagttca | ccatagtttt | tccacacaac | caaaaggaa | actggaaaaa | tgttccttcc | 480 |
| aattaccatt | attgcccgtc | aagctcagat | ttaaattggc | ataatgactt | aataggcaca | 540 |
| gccttacaag | tcaaaatgcc | caagagtcac | aaggctattc | aagcagacgg | ttggatgtgt | 600 |
| catgcttcca | atgggtcac | tacttgtgat | tccgctggt | acggaccgaa | gtatataaca | 660 |
| cattccatcc | gatccttcac | tccatctgta | gaacaatgca | aggaaagcat | gaacaaacg | 720 |
| aaacaaggaa | cttggctgaa | tccaggcttc | cctcctcaaa | gttgtggata | tgcaactgtg | 780 |
| acggatgctg | aagcagcgat | tgtccaggtg | actcctcacc | atgtgcttgt | tgatgaatac | 840 |
| acaggagaat | gggttgattc | acagttcatc | aacggaaaat | gcagcaatga | catatgcccc | 900 |
| actgtccata | actccacaac | ctggcattcc | gactataagg | tcaaagggct | atgtgattct | 960 |
| aacctcattt | ccacggacat | caccttcttc | tcagaggacg | agagctatc | atccctagga | 1020 |
| aaggagggca | gggttcag | agtaactac | tttgcttatg | aaactggaga | caaggcctgc | 1080 |
| aaaatgcagt | actgcaagca | ttggggagtc | agactcccat | caggtgtctg | gttcgagatg | 1140 |
| gctgataagg | atctctttgc | tgcagccaga | ttccctgaat | gcccagaagg | gtcaagtatc | 1200 |
| tctgctccat | ctcagacctc | agtggatgta | agtctcattc | aggacgttga | gaggatcttg | 1260 |
| gattattccc | tctgccaaga | aacctggagc | aaaatcagag | cggtcttcc | catctctcca | 1320 |
| gtggatctca | gctatcttgc | tcctaaaaac | ccaggaaccg | gtcctgtctt | taccataatc | 1380 |
| aatggtaccc | taaaatactt | tgagaccaga | tacatcagag | tcgatattgc | tgctccaatc | 1440 |
| ctctcaagaa | tggtcggaat | gatcagtgga | actaccacag | aaagggaact | gtgggatgac | 1500 |
| tgggctccat | atgaagacgt | ggaaattgga | cccaatggag | ttctgaggac | cagtttagga | 1560 |
| tataagtttc | ctttatatat | gattggacat | ggtatgttgg | actccgatct | tcatcttagc | 1620 |
| tcaaaggctc | aggtgtttga | acatcctcac | attcaagacg | ctgcttcgca | gcttcctgat | 1680 |
| gatgagactt | tatttttggg | tgatactggg | ctatccaaaa | atccaatcga | gtttgtagaa | 1740 |
| ggttggttca | gtagttggaa | gagctctatt | gcctcttttt | tctttatcat | agggttaatc | 1800 |
| attgactat | tcttggttct | ccgagttggt | atttatcttt | gcattaaatt | aaagcacacc | 1860 |
| aagaaaagac | agatttatac | agacatagag | atgaaccgac | ttggaaagta | a | 1911 |

<210> SEQ ID NO 4
<211> LENGTH: 636
<212> TYPE: PRT

-continued

<213> ORGANISM: Artificial Sequence
<220> FEATURE:
<223> OTHER INFORMATION: H2B VSV-G Chimeric Protein Amino Acid Sequence
<220> FEATURE:
<221> NAME/KEY: CHAIN
<222> LOCATION: (1)..(636)

<400> SEQUENCE: 4

```
Met Pro Asp Pro Ser Lys Ser Ala Pro Ala Pro Lys Lys Gly Ser Lys
1               5                   10                  15

Lys Ala Val Thr Lys Ala Gln Lys Lys Asp Gly Lys Lys Arg Lys Arg
                20                  25                  30

Gly Arg Lys Glu Ser Tyr Ser Ile Tyr Val Tyr Lys Val Leu Lys Gln
            35                  40                  45

Val His Pro Asp Thr Gly Ile Ser Ser Lys Ala Met Gly Ile Met Asn
50                  55                  60

Ser Phe Val Asn Asp Ile Phe Glu Arg Ile Ala Ser Glu Ala Ser Arg
65                  70                  75                  80

Leu Ala His Tyr Asn Lys Arg Ser Thr Ile Thr Ser Arg Glu Val Gln
                85                  90                  95

Thr Ala Val Arg Leu Leu Leu Pro Gly Glu Leu Ala Lys His Ala Val
            100                 105                 110

Ser Glu Gly Thr Lys Ala Val Thr Lys Tyr Thr Ser Ser Lys Lys Cys
        115                 120                 125

Leu Leu Tyr Leu Ala Phe Leu Phe Ile Gly Val Asn Cys Lys Phe Thr
130                 135                 140

Ile Val Phe Pro His Asn Gln Lys Gly Asn Trp Lys Asn Val Pro Ser
145                 150                 155                 160

Asn Tyr His Tyr Cys Pro Ser Ser Ser Asp Leu Asn Trp His Asn Asp
                165                 170                 175

Leu Ile Gly Thr Ala Leu Gln Val Lys Met Pro Lys Ser His Lys Ala
            180                 185                 190

Ile Gln Ala Asp Gly Trp Met Cys His Ala Ser Lys Trp Val Thr Thr
        195                 200                 205

Cys Asp Phe Arg Trp Tyr Gly Pro Lys Tyr Ile Thr His Ser Ile Arg
210                 215                 220

Ser Phe Thr Pro Ser Val Glu Gln Cys Lys Glu Ser Ile Glu Gln Thr
225                 230                 235                 240

Lys Gln Gly Thr Trp Leu Asn Pro Gly Phe Pro Pro Gln Ser Cys Gly
                245                 250                 255

Tyr Ala Thr Val Thr Asp Ala Glu Ala Ala Ile Val Gln Val Thr Pro
            260                 265                 270

His His Val Leu Val Asp Glu Tyr Thr Gly Glu Trp Val Asp Ser Gln
        275                 280                 285

Phe Ile Asn Gly Lys Cys Ser Asn Asp Ile Cys Pro Thr Val His Asn
290                 295                 300

Ser Thr Thr Trp His Ser Asp Tyr Lys Val Lys Gly Leu Cys Asp Ser
305                 310                 315                 320

Asn Leu Ile Ser Thr Asp Ile Thr Phe Phe Ser Glu Asp Gly Glu Leu
                325                 330                 335

Ser Ser Leu Gly Lys Glu Gly Thr Gly Phe Arg Ser Asn Tyr Phe Ala
            340                 345                 350

Tyr Glu Thr Gly Asp Lys Ala Cys Lys Met Gln Tyr Cys Lys His Trp
        355                 360                 365

Gly Val Arg Leu Pro Ser Gly Val Trp Phe Glu Met Ala Asp Lys Asp
```

-continued

```
    370                 375                 380

Leu Phe Ala Ala Ala Arg Phe Pro Glu Cys Pro Glu Gly Ser Ser Ile
385                 390                 395                 400

Ser Ala Pro Ser Gln Thr Ser Val Asp Val Ser Leu Ile Gln Asp Val
                405                 410                 415

Glu Arg Ile Leu Asp Tyr Ser Leu Cys Gln Glu Thr Trp Ser Lys Ile
            420                 425                 430

Arg Ala Gly Leu Pro Ile Ser Pro Val Asp Leu Ser Tyr Leu Ala Pro
        435                 440                 445

Lys Asn Pro Gly Thr Gly Pro Val Phe Thr Ile Ile Asn Gly Thr Leu
    450                 455                 460

Lys Tyr Phe Glu Thr Arg Tyr Ile Arg Val Asp Ile Ala Ala Pro Ile
465                 470                 475                 480

Leu Ser Arg Met Val Gly Met Ile Ser Gly Thr Thr Thr Glu Arg Glu
                485                 490                 495

Leu Trp Asp Asp Trp Ala Pro Tyr Glu Asp Val Glu Ile Gly Pro Asn
            500                 505                 510

Gly Val Leu Arg Thr Ser Leu Gly Tyr Lys Phe Pro Leu Tyr Met Ile
        515                 520                 525

Gly His Gly Met Leu Asp Ser Asp Leu His Leu Ser Ser Lys Ala Gln
    530                 535                 540

Val Phe Glu His Pro His Ile Gln Asp Ala Ala Ser Gln Leu Pro Asp
545                 550                 555                 560

Asp Glu Thr Leu Phe Phe Gly Asp Thr Gly Leu Ser Lys Asn Pro Ile
                565                 570                 575

Glu Phe Val Glu Gly Trp Phe Ser Ser Trp Lys Ser Ser Ile Ala Ser
            580                 585                 590

Phe Phe Phe Ile Ile Gly Leu Ile Ile Gly Leu Phe Leu Val Leu Arg
        595                 600                 605

Val Gly Ile Tyr Leu Cys Ile Lys Leu Lys His Thr Lys Lys Arg Gln
    610                 615                 620

Ile Tyr Thr Asp Ile Glu Met Asn Arg Leu Gly Lys
625                 630                 635

<210> SEQ ID NO 5
<211> LENGTH: 1938
<212> TYPE: DNA
<213> ORGANISM: Artificial Sequence
<220> FEATURE:
<223> OTHER INFORMATION: H3 VSV-G Chimeric Protein Nucleotide Sequence
<220> FEATURE:
<221> NAME/KEY: misc_feature
<222> LOCATION: (1)..(1938)

<400> SEQUENCE: 5
atggcccgaa ccaagcagac tgctcgtaaa tccaccggtg ggaaagcccc ccgcaaacag     60
ctggccacga aagctgccag gaaaagcacc ccctctacct gcggggtgaa gcctcatcgc    120
tacaggcctg ggaccgtggc gcttcgagag attcgtcgtt atcagaagtc gaccgagctg    180
ctcatccgga agctgccctt ccagaggttg gtgagggaga tcgcgcagga tttcaacact    240
gacctgaggt ttcagagcgc agccgtcggt gcgctgcagg aggctagcga agcgtacctg    300
gtgggtctgt tggaagatac taacctgtgt gccatccacg ctaagagagt caccatcatg    360
cccaaagaca tccagttggc tcgccggata cggggagaga gagctaagtg ccttttgtac    420
ttagcttttt tattcatcgg ggtgaattgc aagttcacca tagtttttcc acacaaccaa    480
```

-continued

```
aaaggaaact ggaaaaatgt tccttccaat taccattatt gcccgtcaag ctcagattta    540
aattggcata atgacttaat aggcacagcc ttacaagtca aaatgcccaa gagtcacaag    600
gctattcaag cagacggttg gatgtgtcat gcttccaaat gggtcactac ttgtgatttc    660
cgctggtacg gaccgaagta tataacacat tccatccgat ccttcactcc atctgtagaa    720
caatgcaagg aaagcattga acaaacgaaa caaggaactt ggctgaatcc aggcttccct    780
cctcaaagtt gtggatatgc aactgtgacg gatgctgaag cagcgattgt ccaggtgact    840
cctcaccatg tgcttgttga tgaatacaca ggagaatggg ttgattcaca gttcatcaac    900
ggaaaatgca gcaatgacat atgccccact gtccataact ccacaacctg gcattccgac    960
tataaggtca aagggctatg tgattctaac ctcatttcca cggacatcac cttcttctca   1020
gaggacggag agctatcatc cctaggaaag gagggcacag ggttcagaag taactacttt   1080
gcttatgaaa ctggagacaa ggcctgcaaa atgcagtact gcaagcattg gggagtcaga   1140
ctcccatcag gtgtctggtt cgagatggct gataaggatc tctttgctgc agccagattc   1200
cctgaatgcc cagaagggtc aagtatctct gctccatctc agacctcagt ggatgtaagt   1260
ctcattcagg acgttgagag gatcttggat tattccctct gccaagaaac ctggagcaaa   1320
atcagagcgg tcttcccat ctctccagtg gatctcagct atcttgctcc taaaaaccca   1380
ggaaccggtc ctgtctttac cataatcaat ggtaccctaa atactttga ccagatac    1440
atcagagtcg atattgctgc tccaatcctc tcaagaatgg tcggaatgat cagtggaact   1500
accacagaaa gggaactgtg ggatgactgg gctccatatg aagacgtgga aattggaccc   1560
aatggagttc tgaggaccag tttaggtat aagtttcctt tatatatgat tggacatggt   1620
atgttggact ccgatcttca tcttagctca aaggctcagg tgtttgaaca tcctcacatt   1680
caagacgctg cttcgcagct tcctgatgat gagactttat tttttggtga tactgggcta   1740
tccaaaaatc caatcgagtt tgtagaaggt tggttcagta gttggaagag ctctattgcc   1800
tctttttttct ttatcatagg gttaatcatt ggactattct tggttctccg agttggtatt   1860
tatctttgca ttaaattaaa gcacaccaag aaaagacaga tttatacaga catagagatg   1920
aaccgacttg gaaagtaa                                                 1938
```

<210> SEQ ID NO 6
<211> LENGTH: 645
<212> TYPE: PRT
<213> ORGANISM: Artificial Sequence
<220> FEATURE:
<223> OTHER INFORMATION: H3 VSV-G Chimeric Protein Amino Acid Sequence
<220> FEATURE:
<221> NAME/KEY: CHAIN
<222> LOCATION: (1)..(645)

<400> SEQUENCE: 6

```
Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Thr Pro Ser
            20                  25                  30

Thr Cys Gly Val Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
    50                  55                  60

Leu Pro Phe Gln Arg Leu Val Arg Glu Ile Ala Gln Asp Phe Asn Thr
65                  70                  75                  80

Asp Leu Arg Phe Gln Ser Ala Ala Val Gly Ala Leu Gln Glu Ala Ser
```

```
                    85                  90                  95
Glu Ala Tyr Leu Val Gly Leu Leu Glu Asp Thr Asn Leu Cys Ala Ile
            100                 105                 110

His Ala Lys Arg Val Thr Ile Met Pro Lys Asp Ile Gln Leu Ala Arg
            115                 120                 125

Arg Ile Arg Gly Glu Arg Ala Lys Cys Leu Leu Tyr Leu Ala Phe Leu
130                 135                 140

Phe Ile Gly Val Asn Cys Lys Phe Thr Ile Val Phe Pro His Asn Gln
145                 150                 155                 160

Lys Gly Asn Trp Lys Asn Val Pro Ser Asn Tyr His Tyr Cys Pro Ser
                165                 170                 175

Ser Ser Asp Leu Asn Trp His Asn Asp Leu Ile Gly Thr Ala Leu Gln
            180                 185                 190

Val Lys Met Pro Lys Ser His Lys Ala Ile Gln Ala Asp Gly Trp Met
            195                 200                 205

Cys His Ala Ser Lys Trp Val Thr Thr Cys Asp Phe Arg Trp Tyr Gly
210                 215                 220

Pro Lys Tyr Ile Thr His Ser Ile Arg Ser Phe Thr Pro Ser Val Glu
225                 230                 235                 240

Gln Cys Lys Glu Ser Ile Glu Gln Thr Lys Gln Gly Thr Trp Leu Asn
                245                 250                 255

Pro Gly Phe Pro Pro Gln Ser Cys Gly Tyr Ala Thr Val Thr Asp Ala
            260                 265                 270

Glu Ala Ala Ile Val Gln Val Thr Pro His His Val Leu Val Asp Glu
            275                 280                 285

Tyr Thr Gly Glu Trp Val Asp Ser Gln Phe Ile Asn Gly Lys Cys Ser
290                 295                 300

Asn Asp Ile Cys Pro Thr Val His Asn Ser Thr Thr Trp His Ser Asp
305                 310                 315                 320

Tyr Lys Val Lys Gly Leu Cys Asp Ser Asn Leu Ile Ser Thr Asp Ile
                325                 330                 335

Thr Phe Phe Ser Glu Asp Gly Glu Leu Ser Ser Leu Gly Lys Glu Gly
            340                 345                 350

Thr Gly Phe Arg Ser Asn Tyr Phe Ala Tyr Glu Thr Gly Asp Lys Ala
            355                 360                 365

Cys Lys Met Gln Tyr Cys Lys His Trp Gly Val Arg Leu Pro Ser Gly
370                 375                 380

Val Trp Phe Glu Met Ala Asp Lys Asp Leu Phe Ala Ala Ala Arg Phe
385                 390                 395                 400

Pro Glu Cys Pro Glu Gly Ser Ser Ile Ser Ala Pro Ser Gln Thr Ser
                405                 410                 415

Val Asp Val Ser Leu Ile Gln Asp Val Glu Arg Ile Leu Asp Tyr Ser
            420                 425                 430

Leu Cys Gln Glu Thr Trp Ser Lys Ile Arg Ala Gly Leu Pro Ile Ser
            435                 440                 445

Pro Val Asp Leu Ser Tyr Leu Ala Pro Lys Asn Pro Gly Thr Gly Pro
450                 455                 460

Val Phe Thr Ile Ile Asn Gly Thr Leu Lys Tyr Phe Glu Thr Arg Tyr
465                 470                 475                 480

Ile Arg Val Asp Ile Ala Ala Pro Ile Leu Ser Arg Met Val Gly Met
                485                 490                 495

Ile Ser Gly Thr Thr Thr Glu Arg Glu Leu Trp Asp Asp Trp Ala Pro
            500                 505                 510
```

```
Tyr Glu Asp Val Glu Ile Gly Pro Asn Gly Val Leu Arg Thr Ser Leu
            515                 520                 525

Gly Tyr Lys Phe Pro Leu Tyr Met Ile Gly His Gly Met Leu Asp Ser
        530                 535                 540

Asp Leu His Leu Ser Ser Lys Ala Gln Val Phe Glu His Pro His Ile
545                 550                 555                 560

Gln Asp Ala Ala Ser Gln Leu Pro Asp Asp Glu Thr Leu Phe Phe Gly
                565                 570                 575

Asp Thr Gly Leu Ser Lys Asn Pro Ile Glu Phe Val Glu Gly Trp Phe
            580                 585                 590

Ser Ser Trp Lys Ser Ser Ile Ala Ser Phe Phe Ile Ile Gly Leu
        595                 600                 605

Ile Ile Gly Leu Phe Leu Val Leu Arg Val Gly Ile Tyr Leu Cys Ile
    610                 615                 620

Lys Leu Lys His Thr Lys Arg Gln Ile Tyr Thr Asp Ile Glu Met
625                 630                 635                 640

Asn Arg Leu Gly Lys
                645

<210> SEQ ID NO 7
<211> LENGTH: 1842
<212> TYPE: DNA
<213> ORGANISM: Artificial Sequence
<220> FEATURE:
<223> OTHER INFORMATION: H4 VSV-G Chimeric Protein Nucleotide Sequence
<220> FEATURE:
<221> NAME/KEY: misc_feature
<222> LOCATION: (1)..(1842)

<400> SEQUENCE: 7
atgtctggtc gcggcaaagg cggtaaaggt ttgggtaagg aggtgccaa gcgtcaccga      60 aaagtgctgc gggataacat ccaaggcatc accaaaccgg ccattcggcg ccttgctagg    120
cgtggtgggg ttaagcgaat ttccggtttg atttatgagg agactcgtgg cgttctcaag    180
gtgtttctgg agaacgtgat ccgggacgcc gtgacctaca cggagcacgc caagcgcaag    240
actgtcactg ccatggatgt ggtttacgcg ctcaagcgtc aaggacgcac tctgtacggc    300
ttcggcggta gtgccttttt gtacttagct ttttttattca tcggggtgaa ttgcaagttc    360
accatagttt ttccacacaa ccaaaaagga aactggaaaa atgttccttc caattaccat    420
tattgcccgt caagctcaga tttaaattgg cataatgact aataggcac agccttacaa      480 gtcaaaatgc ccaagagtca caaggctatt caagcagacg gttggatgtg tcatgcttcc    540
aaatgggtca ctacttgtga tttccgctgg tacggaccga agtatataac acattccatc    600
cgatccttca ctccatctgt agaacaatgc aaggaaagca ttgaacaaac gaaacaagga    660
acttggctga atccaggctt ccctcctcaa agttgtggat atgcaactgt gacggatgct    720
gaagcagcga ttgtccaggt gactcctcac catgtgcttg ttgatgaata cagggagaa      780 tgggttgatt cacagttcat caacggaaaa tgcagcaatg acatatgccc cactgtccat    840
aactccacaa cctggcattc cgactataag gtcaaagggc tatgtgattc taacctcatt    900
tccacggaca tcaccttctt ctcagaggac ggagagctat catccctagg aaaggagggc    960
acagggttca gaagtaacta ctttgcttat gaaactggag acaaggcctg caaaatgcag   1020
tactgcaagc attggggagt cagactccca tcaggtgtct ggttcgagat ggctgataag   1080
gatctctttg ctgcagccag attccctgaa tgcccagaag ggtcaagtat ctctgctcca   1140
```

```
tctcagacct cagtggatgt aagtctcatt caggacgttg agaggatctt ggattattcc    1200
ctctgccaag aaacctggag caaaatcaga gcgggtcttc ccatctctcc agtggatctc    1260
agctatcttg ctcctaaaaa cccaggaacc ggtcctgtct ttaccataat caatggtacc    1320
ctaaaatact ttgagaccag atacatcaga gtcgatattg ctgctccaat cctctcaaga    1380
atggtcggaa tgatcagtgg aactaccaca gaaagggaac tgtgggatga ctgggctcca    1440
tatgaagacg tggaaattgg acccaatgga gttctgagga ccagtttagg atataagttt    1500
cctttatata tgattggaca tggtatgttg gactccgatc ttcatcttag ctcaaaggct    1560
caggtgtttg aacatcctca cattcaagac gctgcttcgc agcttcctga tgatgagact    1620
ttattttttg gtgatactgg gctatccaaa aatccaatcg agtttgtaga aggttggttc    1680
agtagttgga agagctctat tgcctctttt ttctttatca tagggttaat cattggacta    1740
ttcttggttc tccgagttgg tatttatctt tgcattaaat taaagcacac caagaaaaga    1800
cagatttata cagacataga gatgaaccga cttggaaagt aa                      1842
```

<210> SEQ ID NO 8
<211> LENGTH: 613
<212> TYPE: PRT
<213> ORGANISM: Artificial Sequence
<220> FEATURE:
<223> OTHER INFORMATION: H4 VSV-G Chimeric Protein Amino Acid Sequence
<220> FEATURE:
<221> NAME/KEY: CHAIN
<222> LOCATION: (1)..(613)

<400> SEQUENCE: 8

```
Met Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Gly Leu Ile Tyr Glu Glu Thr Arg Gly Val Leu Lys Val Phe Leu Glu
    50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly Lys Cys Leu Leu Tyr Leu Ala Phe Leu
            100                 105                 110

Phe Ile Gly Val Asn Cys Lys Phe Thr Ile Val Phe Pro His Asn Gln
        115                 120                 125

Lys Gly Asn Trp Lys Asn Val Pro Ser Asn Tyr His Tyr Cys Pro Ser
    130                 135                 140

Ser Ser Asp Leu Asn Trp His Asn Asp Leu Ile Gly Thr Ala Leu Gln
145                 150                 155                 160

Val Lys Met Pro Lys Ser His Lys Ala Ile Gln Ala Asp Gly Trp Met
                165                 170                 175

Cys His Ala Ser Lys Trp Val Thr Thr Cys Asp Phe Arg Trp Tyr Gly
            180                 185                 190

Pro Lys Tyr Ile Thr His Ser Ile Arg Ser Phe Thr Pro Ser Val Glu
        195                 200                 205

Gln Cys Lys Glu Ser Ile Glu Gln Thr Lys Gln Gly Thr Trp Leu Asn
    210                 215                 220
```

Pro Gly Phe Pro Pro Gln Ser Cys Gly Tyr Ala Thr Val Thr Asp Ala
225                 230                 235                 240

Glu Ala Ala Ile Val Gln Val Thr Pro His His Val Leu Val Asp Glu
            245                 250                 255

Tyr Thr Gly Glu Trp Val Asp Ser Gln Phe Ile Asn Gly Lys Cys Ser
        260                 265                 270

Asn Asp Ile Cys Pro Thr Val His Asn Ser Thr Thr Trp His Ser Asp
    275                 280                 285

Tyr Lys Val Lys Gly Leu Cys Asp Ser Asn Leu Ile Ser Thr Asp Ile
290                 295                 300

Thr Phe Phe Ser Glu Asp Gly Glu Leu Ser Ser Leu Gly Lys Glu Gly
305                 310                 315                 320

Thr Gly Phe Arg Ser Asn Tyr Phe Ala Tyr Glu Thr Gly Asp Lys Ala
            325                 330                 335

Cys Lys Met Gln Tyr Cys Lys His Trp Gly Val Arg Leu Pro Ser Gly
        340                 345                 350

Val Trp Phe Glu Met Ala Asp Lys Asp Leu Phe Ala Ala Ala Arg Phe
    355                 360                 365

Pro Glu Cys Pro Glu Gly Ser Ser Ile Ser Ala Pro Ser Gln Thr Ser
370                 375                 380

Val Asp Val Ser Leu Ile Gln Asp Val Glu Arg Ile Leu Asp Tyr Ser
385                 390                 395                 400

Leu Cys Gln Glu Thr Trp Ser Lys Ile Arg Ala Gly Leu Pro Ile Ser
            405                 410                 415

Pro Val Asp Leu Ser Tyr Leu Ala Pro Lys Asn Pro Gly Thr Gly Pro
        420                 425                 430

Val Phe Thr Ile Ile Asn Gly Thr Leu Lys Tyr Phe Glu Thr Arg Tyr
    435                 440                 445

Ile Arg Val Asp Ile Ala Ala Pro Ile Leu Ser Arg Met Val Gly Met
450                 455                 460

Ile Ser Gly Thr Thr Glu Arg Glu Leu Trp Asp Asp Trp Ala Pro
465                 470                 475                 480

Tyr Glu Asp Val Glu Ile Gly Pro Asn Gly Val Leu Arg Thr Ser Leu
            485                 490                 495

Gly Tyr Lys Phe Pro Leu Tyr Met Ile Gly His Gly Met Leu Asp Ser
        500                 505                 510

Asp Leu His Leu Ser Ser Lys Ala Gln Val Phe Glu His Pro His Ile
    515                 520                 525

Gln Asp Ala Ala Ser Gln Leu Pro Asp Glu Thr Leu Phe Gly
530                 535                 540

Asp Thr Gly Leu Ser Lys Asn Pro Ile Glu Phe Val Glu Gly Trp Phe
545                 550                 555                 560

Ser Ser Trp Lys Ser Ser Ile Ala Ser Phe Phe Ile Ile Gly Leu
            565                 570                 575

Ile Ile Gly Leu Phe Leu Val Leu Arg Val Gly Ile Tyr Leu Cys Ile
        580                 585                 590

Lys Leu Lys His Thr Lys Lys Arg Gln Ile Tyr Thr Asp Ile Glu Met
    595                 600                 605

Asn Arg Leu Gly Lys
    610

<210> SEQ ID NO 9
<211> LENGTH: 1977
<212> TYPE: DNA

<213> ORGANISM: Artificial Sequence
<220> FEATURE:
<223> OTHER INFORMATION: SSBP-1 VSV-G Chimeric Protein Nucleotide
      Sequence
<220> FEATURE:
<221> NAME/KEY: misc_feature
<222> LOCATION: (1)..(1977)

<400> SEQUENCE: 9

| | | | | | |
|---|---|---|---|---|---|
| atgtttcgaa | gacctgtatt | acaggtactt | cgtcagtttg | taagacatga gtccgaaaca | 60 |
| actaccagtt | tggttcttga | agatccctg | aatcgtgtgc | acttacttgg gcgagtgggt | 120 |
| caggaccctg | tcttgagaca | ggtggaagga | aaaaatccag | tcacaatatt ttctctagca | 180 |
| actaatgaga | tgtggcgatc | aggggatagt | gaagtttacc | aactgggtga tgtcagtcaa | 240 |
| aagacaacat | ggcacagaat | atcagtattc | cggccaggcc | tcagagacgt ggcatatcaa | 300 |
| tatgtgaaaa | agggtctcg | aatttatttg | gaaggaaaa | tagactatgg tgaatacatg | 360 |
| gataaaaata | atgtgaggcg | acaagcaaca | caatcatag | ctgataatat tatatttctg | 420 |
| agtgaccaga | cgaaagagaa | ggagaagtgc | cttttgtact | tagcttttt attcatcggg | 480 |
| gtgaattgca | agttcaccat | agttttcca | cacaaccaaa | aaggaaactg aaaaatgtt | 540 |
| ccttccaatt | accattattg | cccgtcaagc | tcagatttaa | attggcataa tgacttaata | 600 |
| ggcacagcct | acaagtcaa | aatgcccaag | agtcacaagg | ctattcaagc agacggttgg | 660 |
| atgtgtcatg | cttccaaatg | ggtcactact | tgtgatttcc | gctggtacgg accgaagtat | 720 |
| ataacacatt | ccatccgatc | cttcactcca | tctgtagaac | aatgcaagga agcattgaa | 780 |
| caaacgaaac | aaggaacttg | gctgaatcca | ggcttcctc | ctcaaagttg tggatatgca | 840 |
| actgtgacgg | atgctgaagc | agcgattgtc | caggtgactc | ctcaccatgt gcttgttgat | 900 |
| gaatacacag | gagaatgggt | tgattcacag | ttcatcaacg | aaaatgcag caatgacata | 960 |
| tgccccactg | tccataactc | cacaacctgg | cattccgact | ataaggtcaa agggctatgt | 1020 |
| gattctaacc | tcatttccac | ggacatcacc | ttcttctcag | aggacggaga gctatcatcc | 1080 |
| ctaggaaagg | agggcacagg | gttcagaagt | aactactttg | cttatgaaac tggagacaag | 1140 |
| gcctgcaaaa | tgcagtactg | caagcattgg | ggagtcagac | tcccatcagg tgtctggttc | 1200 |
| gagatggctg | ataaggatct | cttttgctgca | gccagattcc | ctgaatgccc agaagggtca | 1260 |
| agtatctctg | ctccatctca | gacctcagtg | gatgtaagtc | tcattcagga cgttgagagg | 1320 |
| atcttggatt | attccctctg | ccaagaaacc | tggagcaaaa | tcagagcggg tcttcccatc | 1380 |
| tctccagtgg | atctcagcta | tcttgctcct | aaaaacccag | gaaccggtcc tgtctttacc | 1440 |
| ataatcaatg | gtaccctaaa | atactttgag | accagataca | tcagagtcga tattgctgct | 1500 |
| ccaatcctct | caagaatggt | cggaatgatc | agtggaacta | ccacagaaag ggaactgtgg | 1560 |
| gatgactggg | ctccatatga | agacgtggaa | attggaccca | atggagttct gaggaccagt | 1620 |
| ttaggatata | gtttcctttt | atatatgatt | ggacatggta | tgttggactc cgatcttcat | 1680 |
| cttagctcaa | aggctcaggt | gtttgaacat | cctcacattc | aagacgctgc ttcgcagctt | 1740 |
| cctgatgatg | agactttatt | ttttggtgat | actgggctat | ccaaaaatcc aatcgagttt | 1800 |
| gtagaaggtt | ggtcagtag | ttggaagagc | tctattgcct | ctttttttct tatcataggg | 1860 |
| ttaatcattg | gactattctt | ggttctccga | gttggtattt | atctttgcat taaattaaag | 1920 |
| cacaccaaga | aaagacagat | ttatacagac | atagagatga | accgacttgg aaagtaa | 1977 |

<210> SEQ ID NO 10
<211> LENGTH: 658

<212> TYPE: PRT
<213> ORGANISM: Artificial Sequence
<220> FEATURE:
<223> OTHER INFORMATION: SSBP-1 VSV-G Chimeric Protein Amino Acid Sequence
<220> FEATURE:
<221> NAME/KEY: CHAIN
<222> LOCATION: (1)..(658)

<400> SEQUENCE: 10

```
Met Phe Arg Arg Pro Val Leu Gln Val Leu Arg Gln Phe Val Arg His
1               5                   10                  15

Glu Ser Glu Thr Thr Thr Ser Leu Val Leu Glu Arg Ser Leu Asn Arg
            20                  25                  30

Val His Leu Leu Gly Arg Val Gly Gln Asp Pro Val Leu Arg Gln Val
        35                  40                  45

Glu Gly Lys Asn Pro Val Thr Ile Phe Ser Leu Ala Thr Asn Glu Met
    50                  55                  60

Trp Arg Ser Gly Asp Ser Glu Val Tyr Gln Leu Gly Asp Val Ser Gln
65                  70                  75                  80

Lys Thr Thr Trp His Arg Ile Ser Val Phe Arg Pro Gly Leu Arg Asp
                85                  90                  95

Val Ala Tyr Gln Tyr Val Lys Lys Gly Ser Arg Ile Tyr Leu Glu Gly
            100                 105                 110

Lys Ile Asp Tyr Gly Glu Tyr Met Asp Lys Asn Asn Val Arg Arg Gln
        115                 120                 125

Ala Thr Thr Ile Ile Ala Asp Asn Ile Ile Phe Leu Ser Asp Gln Thr
    130                 135                 140

Lys Glu Lys Glu Lys Cys Leu Leu Tyr Leu Ala Phe Leu Phe Ile Gly
145                 150                 155                 160

Val Asn Cys Lys Phe Thr Ile Val Phe Pro His Asn Gln Lys Gly Asn
                165                 170                 175

Trp Lys Asn Val Pro Ser Asn Tyr His Tyr Cys Pro Ser Ser Ser Asp
            180                 185                 190

Leu Asn Trp His Asn Asp Leu Ile Gly Thr Ala Leu Gln Val Lys Met
        195                 200                 205

Pro Lys Ser His Lys Ala Ile Gln Ala Asp Gly Trp Met Cys His Ala
    210                 215                 220

Ser Lys Trp Val Thr Thr Cys Asp Phe Arg Trp Tyr Gly Pro Lys Tyr
225                 230                 235                 240

Ile Thr His Ser Ile Arg Ser Phe Thr Pro Ser Val Glu Gln Cys Lys
                245                 250                 255

Glu Ser Ile Glu Gln Thr Lys Gln Gly Thr Trp Leu Asn Pro Gly Phe
            260                 265                 270

Pro Pro Gln Ser Cys Gly Tyr Ala Thr Val Thr Asp Ala Glu Ala Ala
        275                 280                 285

Ile Val Gln Val Thr Pro His His Val Leu Val Asp Glu Tyr Thr Gly
    290                 295                 300

Glu Trp Val Asp Ser Gln Phe Ile Asn Gly Lys Cys Ser Asn Asp Ile
305                 310                 315                 320

Cys Pro Thr Val His Asn Ser Thr Thr Trp His Ser Asp Tyr Lys Val
                325                 330                 335

Lys Gly Leu Cys Asp Ser Asn Leu Ile Ser Thr Asp Ile Thr Phe Phe
            340                 345                 350

Ser Glu Asp Gly Glu Leu Ser Ser Leu Gly Lys Glu Gly Thr Gly Phe
        355                 360                 365
```

-continued

Arg Ser Asn Tyr Phe Ala Tyr Glu Thr Gly Asp Lys Ala Cys Lys Met
        370

```
ttccccccac ccatgcctcc gtcagcgcaa ggccctcttc cccctgccc aatcaggccg      300 cctttcccca accaccagat gaggcacccc ttcccagttc ctccttgttt tcctcccatg      360
ccaccaccaa tgccttgtcc taataacccc ccagtccctg gggcacctcc tggacaaggc      420
actttcccct tcatgatgcc ccctcccctcc atgcctcatc cccgcccccc tccagtcatg     480
ccgcagcagg ttaattatca gtaccctccg ggctattctc accacaactt cccacctccc      540
agttttaata gtttccagaa caaccctagt tctttcctgc ccagtgctaa taacagcagt      600
agtcctcatt tcagacatct ccctccatac ccactcccaa aggctcccag tgagagaagg      660
tccccagaaa ggctgaaaca ctatgatgac acacaggcacc gagatcacag tcatgggcga     720
ggtgagaggc atcggtccct ggatcggcgg gagcgaggcc gcagtcccga caggagaaga      780
caagacagcc ggtacagatc tgattatgac cgagggagaa caccatctcg ccaccgcagc      840
tacgaacgga gcagagagcg agaacgggag agacacaggc atcgagacaa ccgaagatca      900
ccatctctgg aaaggtccta caaaaaagag tataagagat ctggaaggag ttacggttta      960
tcggttgttc ctgaacctgc tggatgcaca ccagaattac ctggggagat tattaaaaat     1020
acagattctt gggccccacc cctggagatt gtgaatcatc gctccccaag tagggagaag     1080
aagagagctc gttgggagga agaaaaagac cgttggagtg acaaccagag ttctggcaaa     1140
gacaagaact ataccctcaat caaggaaaaa gagcccgagg agaccatgcc tgacaagaat     1200
gaggaggaag aagaagaact tcttaagcct gtgtggattc gatgcactca ttcagaaaac     1260
tactactcca gtgaccccat ggatcaggtg ggagattcta cagtggttgg aacgagtagg     1320
cttcgtgact tatatgacaa atttgaggag gagttgggga gcaggcaaga aaaggccaaa     1380
gctgctcggc ctccgtggga acctccaaag acgaagctcg atgaagattt agagagttcc     1440
agtgaatccg agtgtgagtc tgatgaggac agcacctgtt ctagcagctc agactctgaa     1500
gtttttgacg ttattgcaga aatcaaacgc aaaaaggccc accctgaccg acttcatgat     1560
gaactttggt acaacgatcc aggccagatg aatgatggac cactctgcaa atgcagcgca     1620
aaggcaagac gcacaggaat taggcacagc atttatcctg gagaagaggc catcaagccc     1680
tgtcgtccta tgaccaacaa tgctggcaga cttttccact accggatcac agtctccccg     1740
cctacgaact ttttaactga caggccaact gttatagaat acgatgatca cgagtatatc     1800
tttgaaggat tttctatgtt tgcacatgcc cccctgacca atattccact gtgtaaagta     1860
attagattca acatagacta cacgattcat ttcattgaag agatgatgcc ggagaatttt     1920
tgtgtgaaag gcttgaact ctttttcactg ttcctattca gagatatttt ggaattatat     1980
gactggaatc ttaaaggtcc tttgtttgaa cacagccctc cctgctgccc aagatttcat     2040
ttcatgccac gttttgtaag atttcttcca gatggaggaa aggaagtgct gtccatgcac     2100
cagattctcc tgtacttgtt aaggtgcagc aaagccctgg tgcctgagga ggagattgcc     2160
aatatgcttc agtgggagga gctggagtgg cagaaatatg cagaagaatg caaaggcatg     2220
attgttacca accctgggac gaaaccaagc tctgtccgta tcgatcaact ggatcgtgaa     2280
cagttcaacc ccgatgtgat tacttttccg attatcgtcc actttgggat acgccctgca     2340
cagttgagtt atgcaggaga cccacagtac caaaaactgt ggaagagtta tgtgaaactt     2400
cgccacctcc tagcaaatag tcccaaagtc aaacaaactg acaaacagaa gctggcacag     2460
agggaggaag ccctccaaaa aatacggcag aagaatacaa tgagacgaga gtaacggtg      2520 gagctaagta gccaaggatt ctggaaaact ggcatccgtt ctgatgtctg tcagcatgca     2580
atgatgctac ctgttctgac ccatcatatc cgctaccacc aatgcctaat gcatttggac     2640
```

-continued

```
aagttgatag gatatacttt ccaagatcgt tgtctgttgc agctggccat gactcatcca    2700
agtcatcatt taaattttgg aatgaatcct gatcatgcca ggaattcatt atctaactgt    2760
ggaattcggc agcccaaata cggagacaga aaagttcatc acatgcacat gcggaagaaa    2820
gggattaaca ccttgataaa tatcatgtca cgccttggcc aagatgaccc aactccctcg    2880
aggattaacc acaatgaacg gttggaattc ctgggtgatg ctgttgttga atttctgacc    2940
agcgtccatt tgtactattt gtttcctagt ctggaagaag gaggattagc aacctatcgg    3000
actgccattg ttcagaatca gcaccttgcc atgctagcaa agaaacttga actggatcca    3060
tttatgctgt atgctcacgg gcctgacctt tgtagagaat cggaccttcg acatgcaatg    3120
gccaattgtt ttgaagcgtt aataggagct gtttacttgg agggaagcct ggaggaagcc    3180
aagcagttat ttggacgctt gctctttaat gatccggacc tgcgcgaagt ctggctcaat    3240
tatcctctcc acccactcca actacaagag ccaaatactg atcgacaact tattgaaact    3300
tctccagttc tacaaaaact tactgagttt gaagaagcaa ttggagtaat ttttactcat    3360
gttcgacttc tggcaagggc attcacattg agaactgtgg gatttaacca tctgacccta    3420
ggccacaatc agagaatgga attcctaggt gactccataa tgcaactggt agccacagag    3480
tacttattca ttcatttccc agatcatcat gaaggacact taactttgtt gcgaagctct    3540
ttggtgaata atagaactca ggccaaggta gcggaggagc tgggcatgca ggagtacgcc    3600
ataaccaacg acaagaccaa gaggcctgtg gcgcttcgca ccaagacctt ggcggacctt    3660
ttggaatcat ttattgcagc gctgtacact gataaggatt tggaatatgt tcatactttc    3720
atgaatgtct gcttctttcc acgattgaaa gaattcattt tgaatcagga ttggaatgac    3780
cccaaatccc agcttcagca gtgttgcttg cacttaggaa cagaaggaaa agagccagac    3840
attcctctgt acaagactct gcagacagtg ggcccatccc atgcccgaac ctacactgtg    3900
gctgtttatt tcaagggaga agaataggc tgtgggaaag gaccaagtat tcagcaagcg    3960
gaaatgggag cagcaatgga tgcgcttgaa aaatataatt ttccccagat ggcccatcag    4020
aagcggttca tcgaacggaa gtacagacaa gagttaaaag aaatgaggtg ggaaagagag    4080
catcaagaga gagagccaga tgagactgaa gacatcaaga aaaagtgcct tttgtactta    4140
gctttttttat tcatcggggt gaattgcaag ttcaccatag ttttttccaca caaccaaaaa    4200
ggaaactgga aaaatgttcc ttccaattac cattattgcc cgtcaagctc agatttaaat    4260
tggcataatg acttaatagg cacagcctta caagtcaaaa tgcccaagag tcacaaggct    4320
attcaagcag acggttggat gtgtcatgct tccaaatggg tcactacttg tgatttccgc    4380
tggtacggac cgaagtatat aacacattcc atccgatcct tcactccatc tgtagaacaa    4440
tgcaaggaaa gcattgaaca aacgaaacaa ggaacttggc tgaatccagg cttccctcct    4500
caaagttgtg gatatgcaac tgtgacggat gctgaagcag cgattgtcca ggtgactcct    4560
caccatgtgc ttgttgatga atacacagga gaatgggttg attcacagtt catcaacgga    4620
aaatgcagca atgacatatg ccccactgtc cataactcca caacctggca ttccgactat    4680
aaggtcaaag ggctatgtga ttctaacctc atttccacgg acatcacctt cttctcagag    4740
gacggagagc tatcatccct aggaaaggag ggcacagggt tcagaagtaa ctactttgct    4800
tatgaaactg gagacaaggc ctgcaaaatg cagtactgca agcattgggg agtcagactc    4860
ccatcaggtg tctggttcga gatggctgat aaggatctct ttgctgcagc cagattccct    4920
gaatgcccag aagggtcaag tatctctgct ccatctcaga cctcagtgga tgtaagtctc    4980
```

-continued

```
attcaggacg ttgagaggat cttggattat tccctctgcc aagaaacctg gagcaaaatc    5040
agagcgggtc ttcccatctc tccagtggat ctcagctatc ttgctcctaa aaacccagga    5100
accggtcctg tctttaccat aatcaatggt accctaaaat actttgagac cagatacatc    5160
agagtcgata ttgctgctcc aatcctctca agaatggtcg gaatgatcag tggaactacc    5220
acagaaaggg aactgtggga tgactgggct ccatatgaag acgtggaaat tggacccaat    5280
ggagttctga ggaccagttt aggatataag tttcctttat atatgattgg acatggtatg    5340
ttggactccg atcttcatct tagctcaaag gctcaggtgt tgaacatcc tcacattcaa     5400 gacgctgctt cgcagcttcc tgatgatgag actttatttt ttggtgatac tgggctatcc    5460
aaaaatccaa tcgagtttgt agaaggttgg ttcagtagtt ggaagagctc tattgcctct    5520
tttttcttta tcatagggtt aatcattgga ctattcttgg ttctccgagt tggtatttat    5580
ctttgcatta aattaaagca caccaagaaa agacagattt atacagacat agagatgaac    5640
cgacttggaa agtaa                                                     5655
```

```
<210> SEQ ID NO 12
<211> LENGTH: 1884
<212> TYPE: PRT
<213> ORGANISM: Artificial Sequence
<220> FEATURE:
<223> OTHER INFORMATION: RNase III VSV-G Chimeric Protein with VSV-G at
      C-terminal Amino Acid Sequence

<400> SEQUENCE: 12
```

```
Met Met Gln Gly Asn Thr Cys His Arg Met Ser Phe His Pro Gly Arg
1               5                   10                  15

Gly Cys Pro Arg Gly Arg Gly Gly His Gly Ala Arg Pro Ser Ala Pro
            20                  25                  30

Ser Phe Arg Pro Gln Asn Leu Arg Leu Leu His Pro Gln Gln Pro Pro
        35                  40                  45

Val Gln Tyr Gln Tyr Glu Pro Pro Ser Ala Pro Ser Thr Thr Phe Ser
    50                  55                  60

Asn Ser Pro Ala Pro Asn Phe Leu Pro Pro Arg Pro Asp Phe Val Pro
65                  70                  75                  80

Phe Pro Pro Pro Met Pro Pro Ser Ala Gln Gly Pro Leu Pro Pro Cys
                85                  90                  95

Pro Ile Arg Pro Pro Phe Pro Asn His Gln Met Arg His Pro Phe Pro
            100                 105                 110

Val Pro Pro Cys Phe Pro Pro Met Pro Pro Met Pro Cys Pro Asn
        115                 120                 125

Asn Pro Pro Val Pro Gly Ala Pro Gly Gln Gly Thr Phe Pro Phe
    130                 135                 140

Met Met Pro Pro Ser Met Pro His Pro Pro Pro Pro Val Met
145                 150                 155                 160

Pro Gln Gln Val Asn Tyr Gln Tyr Pro Pro Gly Tyr Ser His His Asn
                165                 170                 175

Phe Pro Pro Pro Ser Phe Asn Ser Phe Gln Asn Asn Pro Ser Ser Phe
            180                 185                 190

Leu Pro Ser Ala Asn Asn Ser Ser Pro His Phe Arg His Leu Pro
        195                 200                 205

Pro Tyr Pro Leu Pro Lys Ala Pro Ser Glu Arg Ser Pro Glu Arg
    210                 215                 220

Leu Lys His Tyr Asp Asp His Arg His Arg Asp His Ser His Gly Arg
225                 230                 235                 240
```

-continued

```
Gly Glu Arg His Arg Ser Leu Asp Arg Arg Glu Arg Gly Arg Ser Pro
                245                 250                 255
Asp Arg Arg Arg Gln Asp Ser Arg Tyr Arg Ser Asp Tyr Asp Arg Gly
            260                 265                 270
Arg Thr Pro Ser Arg His Arg Ser Tyr Glu Arg Ser Arg Glu Arg Glu
        275                 280                 285
Arg Glu Arg His Arg His Arg Asp Asn Arg Arg Ser Pro Ser Leu Glu
    290                 295                 300
Arg Ser Tyr Lys Lys Glu Tyr Lys Arg Ser Gly Arg Ser Tyr Gly Leu
305                 310                 315                 320
Ser Val Val Pro Glu Pro Ala Gly Cys Thr Pro Glu Leu Pro Gly Glu
                325                 330                 335
Ile Ile Lys Asn Thr Asp Ser Trp Ala Pro Leu Glu Ile Val Asn
            340                 345                 350
His Arg Ser Pro Ser Arg Glu Lys Lys Arg Ala Arg Trp Glu Glu Glu
        355                 360                 365
Lys Asp Arg Trp Ser Asp Asn Gln Ser Ser Gly Lys Asp Lys Asn Tyr
    370                 375                 380
Thr Ser Ile Lys Glu Lys Glu Pro Glu Glu Thr Met Pro Asp Lys Asn
385                 390                 395                 400
Glu Glu Glu Glu Glu Glu Leu Leu Lys Pro Val Trp Ile Arg Cys Thr
                405                 410                 415
His Ser Glu Asn Tyr Tyr Ser Ser Asp Pro Met Asp Gln Val Gly Asp
            420                 425                 430
Ser Thr Val Val Gly Thr Ser Arg Leu Arg Asp Leu Tyr Asp Lys Phe
        435                 440                 445
Glu Glu Glu Leu Gly Ser Arg Gln Glu Lys Ala Lys Ala Ala Arg Pro
    450                 455                 460
Pro Trp Glu Pro Pro Lys Thr Lys Leu Asp Glu Asp Leu Glu Ser Ser
465                 470                 475                 480
Ser Glu Ser Glu Cys Glu Ser Asp Glu Asp Ser Thr Cys Ser Ser Ser
                485                 490                 495
Ser Asp Ser Glu Val Phe Asp Val Ile Ala Glu Ile Lys Arg Lys Lys
            500                 505                 510
Ala His Pro Asp Arg Leu His Asp Glu Leu Trp Tyr Asn Asp Pro Gly
        515                 520                 525
Gln Met Asn Asp Gly Pro Leu Cys Lys Cys Ser Ala Lys Ala Arg Arg
    530                 535                 540
Thr Gly Ile Arg His Ser Ile Tyr Pro Gly Glu Glu Ala Ile Lys Pro
545                 550                 555                 560
Cys Arg Pro Met Thr Asn Asn Ala Gly Arg Leu Phe His Tyr Arg Ile
                565                 570                 575
Thr Val Ser Pro Pro Thr Asn Phe Leu Thr Asp Arg Pro Thr Val Ile
            580                 585                 590
Glu Tyr Asp Asp His Glu Tyr Ile Phe Glu Gly Phe Ser Met Phe Ala
        595                 600                 605
His Ala Pro Leu Thr Asn Ile Pro Leu Cys Lys Val Ile Arg Phe Asn
    610                 615                 620
Ile Asp Tyr Thr Ile His Phe Ile Glu Glu Met Met Pro Glu Asn Phe
625                 630                 635                 640
Cys Val Lys Gly Leu Glu Leu Phe Ser Leu Phe Leu Phe Arg Asp Ile
                645                 650                 655
```

-continued

Leu Glu Leu Tyr Asp Trp Asn Leu Lys Gly Pro Leu Phe Glu Asp Ser
            660                 665                 670

Pro Pro Cys Cys Pro Arg Phe His Phe Met Pro Arg Phe Val Arg Phe
            675                 680                 685

Leu Pro Asp Gly Gly Lys Glu Val Leu Ser Met His Gln Ile Leu Leu
            690                 695                 700

Tyr Leu Leu Arg Cys Ser Lys Ala Leu Val Pro Glu Glu Ile Ala
705                 710                 715                 720

Asn Met Leu Gln Trp Glu Glu Leu Glu Trp Gln Lys Tyr Ala Glu Glu
                725                 730                 735

Cys Lys Gly Met Ile Val Thr Asn Pro Gly Thr Lys Pro Ser Ser Val
            740                 745                 750

Arg Ile Asp Gln Leu Asp Arg Glu Gln Phe Asn Pro Asp Val Ile Thr
            755                 760                 765

Phe Pro Ile Ile Val His Phe Gly Ile Arg Pro Ala Gln Leu Ser Tyr
            770                 775                 780

Ala Gly Asp Pro Gln Tyr Gln Lys Leu Trp Lys Ser Tyr Val Lys Leu
785                 790                 795                 800

Arg His Leu Leu Ala Asn Ser Pro Lys Val Lys Gln Thr Asp Lys Gln
                805                 810                 815

Lys Leu Ala Gln Arg Glu Glu Ala Leu Gln Lys Ile Arg Gln Lys Asn
            820                 825                 830

Thr Met Arg Arg Glu Val Thr Val Glu Leu Ser Ser Gln Gly Phe Trp
            835                 840                 845

Lys Thr Gly Ile Arg Ser Asp Val Cys Gln His Ala Met Met Leu Pro
850                 855                 860

Val Leu Thr His His Ile Arg Tyr His Gln Cys Leu Met His Leu Asp
865                 870                 875                 880

Lys Leu Ile Gly Tyr Thr Phe Gln Asp Arg Cys Leu Gln Leu Ala
                885                 890                 895

Met Thr His Pro Ser His His Leu Asn Phe Gly Met Asn Pro Asp His
            900                 905                 910

Ala Arg Asn Ser Leu Ser Asn Cys Gly Ile Arg Gln Pro Lys Tyr Gly
            915                 920                 925

Asp Arg Lys Val His His Met His Met Arg Lys Lys Gly Ile Asn Thr
            930                 935                 940

Leu Ile Asn Ile Met Ser Arg Leu Gly Gln Asp Asp Pro Thr Pro Ser
945                 950                 955                 960

Arg Ile Asn His Asn Glu Arg Leu Glu Phe Leu Gly Asp Ala Val Val
                965                 970                 975

Glu Phe Leu Thr Ser Val His Leu Tyr Tyr Leu Phe Pro Ser Leu Glu
            980                 985                 990

Glu Gly Gly Leu Ala Thr Tyr Arg Thr Ala Ile Val Gln Asn Gln His
            995                 1000                1005

Leu Ala Met Leu Ala Lys Lys Leu Glu Leu Asp Pro Phe Met Leu
    1010                1015                1020

Tyr Ala His Gly Pro Asp Leu Cys Arg Glu Ser Asp Leu Arg His
    1025                1030                1035

Ala Met Ala Asn Cys Phe Glu Ala Leu Ile Gly Ala Val Tyr Leu
    1040                1045                1050

Glu Gly Ser Leu Glu Glu Ala Lys Gln Leu Phe Gly Arg Leu Leu
    1055                1060                1065

Phe Asn Asp Pro Asp Leu Arg Glu Val Trp Leu Asn Tyr Pro Leu

```
            1070                1075                1080
His Pro Leu Gln Leu Gln Glu Pro Asn Thr Asp Arg Gln Leu Ile
    1085                1090                1095
Glu Thr Ser Pro Val Leu Gln Lys Leu Thr Glu Phe Glu Glu Ala
    1100                1105                1110
Ile Gly Val Ile Phe Thr His Val Arg Leu Leu Ala Arg Ala Phe
    1115                1120                1125
Thr Leu Arg Thr Val Gly Phe Asn His Leu Thr Leu Gly His Asn
    1130                1135                1140
Gln Arg Met Glu Phe Leu Gly Asp Ser Ile Met Gln Leu Val Ala
    1145                1150                1155
Thr Glu Tyr Leu Phe Ile His Phe Pro Asp His His Glu Gly His
    1160                1165                1170
Leu Thr Leu Leu Arg Ser Ser Leu Val Asn Asn Arg Thr Gln Ala
    1175                1180                1185
Lys Val Ala Glu Glu Leu Gly Met Gln Glu Tyr Ala Ile Thr Asn
    1190                1195                1200
Asp Lys Thr Lys Arg Pro Val Ala Leu Arg Thr Lys Thr Leu Ala
    1205                1210                1215
Asp Leu Leu Glu Ser Phe Ile Ala Ala Leu Tyr Thr Asp Lys Asp
    1220                1225                1230
Leu Glu Tyr Val His Thr Phe Met Asn Val Cys Phe Phe Pro Arg
    1235                1240                1245
Leu Lys Glu Phe Ile Leu Asn Gln Asp Trp Asn Asp Pro Lys Ser
    1250                1255                1260
Gln Leu Gln Gln Cys Cys Leu Thr Leu Arg Thr Glu Gly Lys Glu
    1265                1270                1275
Pro Asp Ile Pro Leu Tyr Lys Thr Leu Gln Thr Val Gly Pro Ser
    1280                1285                1290
His Ala Arg Thr Tyr Thr Val Ala Val Tyr Phe Lys Gly Glu Arg
    1295                1300                1305
Ile Gly Cys Gly Lys Gly Pro Ser Ile Gln Gln Ala Glu Met Gly
    1310                1315                1320
Ala Ala Met Asp Ala Leu Glu Lys Tyr Asn Phe Pro Gln Met Ala
    1325                1330                1335
His Gln Lys Arg Phe Ile Glu Arg Lys Tyr Arg Gln Glu Leu Lys
    1340                1345                1350
Glu Met Arg Trp Glu Arg Glu His Gln Glu Arg Glu Pro Asp Glu
    1355                1360                1365
Thr Glu Asp Ile Lys Lys Lys Cys Leu Leu Tyr Leu Ala Phe Leu
    1370                1375                1380
Phe Ile Gly Val Asn Cys Lys Phe Thr Ile Val Phe Pro His Asn
    1385                1390                1395
Gln Lys Gly Asn Trp Lys Asn Val Pro Ser Asn Tyr His Tyr Cys
    1400                1405                1410
Pro Ser Ser Ser Asp Leu Asn Trp His Asn Asp Leu Ile Gly Thr
    1415                1420                1425
Ala Leu Gln Val Lys Met Pro Lys Ser His Lys Ala Ile Gln Ala
    1430                1435                1440
Asp Gly Trp Met Cys His Ala Ser Lys Trp Val Thr Thr Cys Asp
    1445                1450                1455
Phe Arg Trp Tyr Gly Pro Lys Tyr Ile Thr His Ser Ile Arg Ser
    1460                1465                1470
```

-continued

```
Phe Thr Pro Ser Val Glu Gln Cys Lys Glu Ser Ile Glu Gln Thr
    1475                1480                1485
Lys Gln Gly Thr Trp Leu Asn Pro Gly Phe Pro Pro Gln Ser Cys
    1490                1495                1500
Gly Tyr Ala Thr Val Thr Asp Ala Glu Ala Ala Ile Val Gln Val
    1505                1510                1515
Thr Pro His His Val Leu Val Asp Glu Tyr Thr Gly Glu Trp Val
    1520                1525                1530
Asp Ser Gln Phe Ile Asn Gly Lys Cys Ser Asn Asp Ile Cys Pro
    1535                1540                1545
Thr Val His Asn Ser Thr Thr Trp His Ser Asp Tyr Lys Val Lys
    1550                1555                1560
Gly Leu Cys Asp Ser Asn Leu Ile Ser Thr Asp Ile Thr Phe Phe
    1565                1570                1575
Ser Glu Asp Gly Glu Leu Ser Ser Leu Gly Lys Glu Gly Thr Gly
    1580                1585                1590
Phe Arg Ser Asn Tyr Phe Ala Tyr Glu Thr Gly Asp Lys Ala Cys
    1595                1600                1605
Lys Met Gln Tyr Cys Lys His Trp Gly Val Arg Leu Pro Ser Gly
    1610                1615                1620
Val Trp Phe Glu Met Ala Asp Lys Asp Leu Phe Ala Ala Ala Arg
    1625                1630                1635
Phe Pro Glu Cys Pro Glu Gly Ser Ser Ile Ser Ala Pro Ser Gln
    1640                1645                1650
Thr Ser Val Asp Val Ser Leu Ile Gln Asp Val Glu Arg Ile Leu
    1655                1660                1665
Asp Tyr Ser Leu Cys Gln Glu Thr Trp Ser Lys Ile Arg Ala Gly
    1670                1675                1680
Leu Pro Ile Ser Pro Val Asp Leu Ser Tyr Leu Ala Pro Lys Asn
    1685                1690                1695
Pro Gly Thr Gly Pro Val Phe Thr Ile Ile Asn Gly Thr Leu Lys
    1700                1705                1710
Tyr Phe Glu Thr Arg Tyr Ile Arg Val Asp Ile Ala Ala Pro Ile
    1715                1720                1725
Leu Ser Arg Met Val Gly Met Ile Ser Gly Thr Thr Thr Glu Arg
    1730                1735                1740
Glu Leu Trp Asp Asp Trp Ala Pro Tyr Glu Asp Val Glu Ile Gly
    1745                1750                1755
Pro Asn Gly Val Leu Arg Thr Ser Leu Gly Tyr Lys Phe Pro Leu
    1760                1765                1770
Tyr Met Ile Gly His Gly Met Leu Asp Ser Asp Leu His Leu Ser
    1775                1780                1785
Ser Lys Ala Gln Val Phe Glu His Pro His Ile Gln Asp Ala Ala
    1790                1795                1800
Ser Gln Leu Pro Asp Asp Glu Thr Leu Phe Phe Gly Asp Thr Gly
    1805                1810                1815
Leu Ser Lys Asn Pro Ile Glu Phe Val Glu Gly Trp Phe Ser Ser
    1820                1825                1830
Trp Lys Ser Ser Ile Ala Ser Phe Phe Phe Ile Ile Gly Leu Ile
    1835                1840                1845
Ile Gly Leu Phe Leu Val Leu Arg Val Gly Ile Tyr Leu Cys Ile
    1850                1855                1860
```

| Lys | Leu | Lys | His | Thr | Lys | Lys | Arg | Gln | Ile | Tyr | Thr | Asp | Ile | Glu |
|---|---|---|---|---|---|---|---|---|---|---|---|---|---|---|
| 1865 | | | | 1870 | | | | | 1875 | | | | | |

| Met | Asn | Arg | Leu | Gly | Lys |
|---|---|---|---|---|---|
| 1880 | | | | | |

<210> SEQ ID NO 13
<211> LENGTH: 3501
<212> TYPE: DNA
<213> ORGANISM: Artificial Sequence
<220> FEATURE:
<223> OTHER INFORMATION: Partial RNase III VSV-G Chimeric Protein with VSV-G at N-terminal Nucleotide Sequence
<220> FEATURE:
<221> NAME/KEY: misc_feature
<222> LOCATION: (1)..(3501)

<400> SEQUENCE: 13

```
atgaagtgcc ttttgtactt agcttttta ttcatcgggg tgaattgcaa gttcaccata    60
gttttccac acaaccaaaa aggaaactgg aaaaatgttc cttccaatta ccattattgc   120
ccgtcaagct cagatttaaa ttggcataat gacttaatag cacagcctt acaagtcaaa   180
atgcccaaga gtcacaaggc tattcaagca gacggttgga tgtgtcatgc ttccaaatgg   240
gtcactactt gtgatttccg ctggtacgga ccgaagtata taacacattc catccgatcc   300
ttcactccat ctgtagaaca atgcaaggaa agcattgaac aaacgaaaca aggaacttgg   360
ctgaatccag gcttccctcc tcaaagttgt ggatatgcaa ctgtgacgga tgctgaagca   420
gcgattgtcc aggtgactcc tcaccatgtg cttgttgatg aatacacagg agaatgggtt   480
gattcacagt tcatcaacgg aaaatgcagc aatgacatat gccccactgt ccataactcc   540
acaacctggc attccgacta taaggtcaaa gggctatgtg attctaacct catttccacg   600
gacatcacct tcttctcaga ggacggagag ctatcatccc taggaaagga gggcacaggg   660
ttcagaagta actactttgc ttatgaaact ggagacaagg cctgcaaaat gcagtactgc   720
aagcattggg gagtcagact cccatcaggt gtctggttcg agatggctga taaggatctc   780
tttgctgcag ccagattccc tgaatgccca gaagggtcaa gtatctctgc tccatctcag   840
acctcagtgg atgtaagtct cattcaggac gttgagagga tcttggatta ttccctctgc   900
caagaaacct ggagcaaaat cagagcgggt cttcccatct ctccagtgga tctcagctat   960
cttgctccta aaacccagg aaccggtcct gtctttacca atcaatgg tacccctaaaa   1020
tactttgaga ccagatacat cagagtcgat attgctgctc caatcctctc aagaatggtc  1080
ggaatgatca gtggaactac cacagaaagg gaactgtggg atgactgggc tccatatgaa  1140
gacgtggaaa ttggacccaa tggagttctg aggaccagtt taggatataa gtttcctta   1200
tatatgattg acatggtat gttggactcc gatcttcatc ttagctcaaa ggctcaggtg  1260
tttgaacatc ctcacattca agacgctgct tcgcagcttc ctgatgatga actttattt   1320
tttggtgata ctgggctatc caaaaatcca atcgagtttg tagaaggttg gttcagtagt  1380
tggaagagct ctattgcctc ttttttcttt atcatagggt taatcattgg actattcttg  1440
gttctccgag ttggtattta tctttgcatt aaattaaagc acaccaagaa aagacagatt  1500
tatacagaca tagagatgaa ccgacttgga aaggccaata tgcttcagtg ggaggagctg  1560
gagtggcaga aatatgcaga agaatgcaaa ggcatgattg ttaccaaccc tgggacgaaa  1620
ccaagctctg tccgtatcga tcaactggat cgtgaacagt tcaaccccga tgtgattact  1680
tttccgatta tcgtccactt tgggatacgc cctgcacagt tgagttatgc aggagaccca  1740
cagtaccaaa aactgtggaa gagttatgtg aaacttcgcc acctcctagc aaatagtccc  1800
```

```
aaagtcaaac aaactgacaa acagaagctg gcacagaggg aggaagccct ccaaaaaata    1860
cggcagaaga atacaatgag acgagaagta acggtggagc taagtagcca aggattctgg    1920
aaaactggca tccgttctga tgtctgtcag catgcaatga tgctacctgt tctgacccat    1980
catatccgct accaccaatg cctaatgcat ttggacaagt tgataggata tactttccaa    2040
gatcgttgtc tgttgcagct ggccatgact catccaagtc atcatttaaa ttttggaatg    2100
aatcctgatc atgccaggaa ttcattatct aactgtggaa ttcggcagcc caaatacgga    2160
gacagaaaag ttcatcacat gcacatgcgg aagaaggga ttaacacctt gataaatatc      2220
atgtcacgcc ttggccaaga tgacccaact ccctcgagga ttaaccacaa tgaacggttg    2280
gaattcctgg gtgatgctgt tgttgaattt ctgaccagcg tccatttgta ctatttgttt    2340
cctagtctgg aagaaggagg attagcaacc tatcggactg ccattgttca gaatcagcac    2400
cttgccatgc tagcaaagaa acttgaactg gatccattta tgctgtatgc tcacgggcct    2460
gacctttgta gagaatcgga ccttcgacat gcaatggcca attgttttga agcgttaata    2520
ggagctgttt acttggaggg aagcctggag gaagccaagc agttatttgg acgcttgctc    2580
tttaatgatc cggacctgcg cgaagtctgg ctcaattatc ctctccaccc actccaacta    2640
caagagccaa atactgatcg acaacttatt gaaacttctc cagttctaca aaaacttact    2700
gagtttgaag aagcaattgg agtaattttt actcatgttc gacttctggc aagggcattc    2760
acattgagaa ctgtgggatt taaccatctg accctaggcc acaatcagag aatggaattc    2820
ctaggtgact ccataatgca actggtagcc acagagtact tattcattca tttcccagat    2880
catcatgaag gacacttaac tttgttgcga agctctttgg tgaataatag aactcaggcc    2940
aaggtagcgg aggagctggg catgcaggag tacgccataa ccaacgacaa gaccaagagg    3000
cctgtggcgc ttcgcaccaa gaccttggcg gaccttttgg aatcatttat tgcagcgctg    3060
tacactgata aggatttgga atatgttcat actttcatga atgtctgctt ctttccacga    3120
ttgaaagaat tcattttgaa tcaggattgg aatgacccca atcccagct tcagcagtgt     3180 tgcttgacac ttaggacaga aggaaaagag ccagacattc tctgtacaa gactctgcag      3240 acagtgggcc catcccatgc ccgaacctac actgtggctg tttatttcaa gggagaaaga    3300
ataggctgtg ggaaaggacc aagtattcag caagcggaaa tgggagcagc aatggatgcg    3360
cttgaaaaat ataattttcc ccagatggcc catcagaagc ggttcatcga acggaagtac    3420
agacaagagt taaagaaat gaggtgggaa agagagcatc aagagagaga gccagatgag     3480
actgaagaca tcaagaaata a                                              3501
```

<210> SEQ ID NO 14
<211> LENGTH: 1166
<212> TYPE: PRT
<213> ORGANISM: Artificial Sequence
<220> FEATURE:
<223> OTHER INFORMATION: Partial RNase III VSV-G Chimeric Protein with
      VSV-G at N-terminal Amino Acid Sequence
<220> FEATURE:
<221> NAME/KEY: CHAIN
<222> LOCATION: (1)..(1166)

<400> SEQUENCE: 14

Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
                20                  25                  30

```
Val Pro Ser Asn Tyr His Tyr Cys Pro Ser Ser Asp Leu Asn Trp
         35                  40                  45
His Asn Asp Leu Ile Gly Thr Ala Leu Gln Val Lys Met Pro Lys Ser
 50                      55                  60
His Lys Ala Ile Gln Ala Asp Gly Trp Met Cys His Ala Ser Lys Trp
 65                  70                  75                  80
Val Thr Thr Cys Asp Phe Arg Trp Tyr Gly Pro Lys Tyr Ile Thr His
                 85                  90                  95
Ser Ile Arg Ser Phe Thr Pro Ser Val Glu Gln Cys Lys Glu Ser Ile
             100                 105                 110
Glu Gln Thr Lys Gln Gly Thr Trp Leu Asn Pro Gly Phe Pro Pro Gln
         115                 120                 125
Ser Cys Gly Tyr Ala Thr Val Thr Asp Ala Glu Ala Ile Val Gln
     130                 135                 140
Val Thr Pro His His Val Leu Val Asp Glu Tyr Thr Gly Glu Trp Val
145                 150                 155                 160
Asp Ser Gln Phe Ile Asn Gly Lys Cys Ser Asn Asp Ile Cys Pro Thr
                 165                 170                 175
Val His Asn Ser Thr Thr Trp His Ser Asp Tyr Lys Val Lys Gly Leu
             180                 185                 190
Cys Asp Ser Asn Leu Ile Ser Thr Asp Ile Thr Phe Phe Ser Glu Asp
         195                 200                 205
Gly Glu Leu Ser Ser Leu Gly Lys Glu Gly Thr Gly Phe Arg Ser Asn
     210                 215                 220
Tyr Phe Ala Tyr Glu Thr Gly Asp Lys Ala Cys Lys Met Gln Tyr Cys
225                 230                 235                 240
Lys His Trp Gly Val Arg Leu Pro Ser Gly Val Trp Phe Glu Met Ala
                 245                 250                 255
Asp Lys Asp Leu Phe Ala Ala Ala Arg Phe Pro Glu Cys Pro Glu Gly
             260                 265                 270
Ser Ser Ile Ser Ala Pro Ser Gln Thr Ser Val Asp Val Ser Leu Ile
         275                 280                 285
Gln Asp Val Glu Arg Ile Leu Asp Tyr Ser Leu Cys Gln Glu Thr Trp
     290                 295                 300
Ser Lys Ile Arg Ala Gly Leu Pro Ile Ser Pro Val Asp Leu Ser Tyr
305                 310                 315                 320
Leu Ala Pro Lys Asn Pro Gly Thr Gly Pro Val Phe Thr Ile Ile Asn
                 325                 330                 335
Gly Thr Leu Lys Tyr Phe Glu Thr Arg Tyr Ile Arg Val Asp Ile Ala
             340                 345                 350
Ala Pro Ile Leu Ser Arg Met Val Gly Met Ile Ser Gly Thr Thr Thr
         355                 360                 365
Glu Arg Glu Leu Trp Asp Asp Trp Ala Pro Tyr Glu Asp Val Glu Ile
     370                 375                 380
Gly Pro Asn Gly Val Leu Arg Thr Ser Leu Gly Tyr Lys Phe Pro Leu
385                 390                 395                 400
Tyr Met Ile Gly His Gly Met Leu Asp Ser Asp Leu His Leu Ser Ser
                 405                 410                 415
Lys Ala Gln Val Phe Glu His Pro His Ile Gln Asp Ala Ala Ser Gln
             420                 425                 430
Leu Pro Asp Asp Glu Thr Leu Phe Phe Gly Asp Thr Gly Leu Ser Lys
         435                 440                 445
Asn Pro Ile Glu Phe Val Glu Gly Trp Phe Ser Ser Trp Lys Ser Ser
```

```
            450             455             460
Ile Ala Ser Phe Phe Phe Ile Ile Gly Leu Ile Ile Gly Leu Phe Leu
465                 470                 475                 480

Val Leu Arg Val Gly Ile Tyr Leu Cys Ile Lys Leu Lys His Thr Lys
                    485                 490                 495

Lys Arg Gln Ile Tyr Thr Asp Ile Glu Met Asn Arg Leu Gly Lys Ala
                500                 505                 510

Asn Met Leu Gln Trp Glu Glu Leu Glu Trp Gln Lys Tyr Ala Glu Glu
            515                 520                 525

Cys Lys Gly Met Ile Val Thr Asn Pro Gly Thr Lys Pro Ser Ser Val
            530                 535                 540

Arg Ile Asp Gln Leu Asp Arg Glu Gln Phe Asn Pro Asp Val Ile Thr
545                 550                 555                 560

Phe Pro Ile Ile Val His Phe Gly Ile Arg Pro Ala Gln Leu Ser Tyr
                    565                 570                 575

Ala Gly Asp Pro Gln Tyr Gln Lys Leu Trp Lys Ser Tyr Val Lys Leu
                580                 585                 590

Arg His Leu Leu Ala Asn Ser Pro Lys Val Lys Gln Thr Asp Lys Gln
            595                 600                 605

Lys Leu Ala Gln Arg Glu Glu Ala Leu Gln Lys Ile Arg Gln Lys Asn
            610                 615                 620

Thr Met Arg Arg Glu Val Thr Val Glu Leu Ser Ser Gln Gly Phe Trp
625                 630                 635                 640

Lys Thr Gly Ile Arg Ser Asp Val Cys Gln His Ala Met Met Leu Pro
                    645                 650                 655

Val Leu Thr His His Ile Arg Tyr His Gln Cys Leu Met His Leu Asp
                660                 665                 670

Lys Leu Ile Gly Tyr Thr Phe Gln Asp Arg Cys Leu Leu Gln Leu Ala
            675                 680                 685

Met Thr His Pro Ser His His Leu Asn Phe Gly Met Asn Pro Asp His
            690                 695                 700

Ala Arg Asn Ser Leu Ser Asn Cys Gly Ile Arg Gln Pro Lys Tyr Gly
705                 710                 715                 720

Asp Arg Lys Val His His Met His Met Arg Lys Lys Gly Ile Asn Thr
                    725                 730                 735

Leu Ile Asn Ile Met Ser Arg Leu Gly Gln Asp Asp Pro Thr Pro Ser
                740                 745                 750

Arg Ile Asn His Asn Glu Arg Leu Glu Phe Leu Gly Asp Ala Val Val
            755                 760                 765

Glu Phe Leu Thr Ser Val His Leu Tyr Tyr Leu Phe Pro Ser Leu Glu
770                 775                 780

Glu Gly Gly Leu Ala Thr Tyr Arg Thr Ala Ile Val Gln Asn Gln His
785                 790                 795                 800

Leu Ala Met Leu Ala Lys Lys Leu Glu Leu Asp Pro Phe Met Leu Tyr
                    805                 810                 815

Ala His Gly Pro Asp Leu Cys Arg Glu Ser Asp Leu Arg His Ala Met
                820                 825                 830

Ala Asn Cys Phe Glu Ala Leu Ile Gly Ala Val Tyr Leu Glu Gly Ser
            835                 840                 845

Leu Glu Glu Ala Lys Gln Leu Phe Gly Arg Leu Leu Phe Asn Asp Pro
850                 855                 860

Asp Leu Arg Glu Val Trp Leu Asn Tyr Pro Leu His Pro Leu Gln Leu
865                 870                 875                 880
```

-continued

Gln Glu Pro Asn Thr Asp Arg Gln Leu Ile Glu Thr Ser Pro Val Leu
                885                 890                 895

Gln Lys Leu Thr Glu Phe Glu Glu Ala Ile Gly Val Ile Phe Thr His
            900                 905                 910

Val Arg Leu Leu Ala Arg Ala Phe Thr Leu Arg Thr Val Gly Phe Asn
        915                 920                 925

His Leu Thr Leu Gly His Asn Gln Arg Met Glu Phe Leu Gly Asp Ser
    930                 935                 940

Ile Met Gln Leu Val Ala Thr Glu Tyr Leu Phe Ile His Phe Pro Asp
945                 950                 955                 960

His His Glu Gly His Leu Thr Leu Leu Arg Ser Ser Leu Val Asn Asn
                965                 970                 975

Arg Thr Gln Ala Lys Val Ala Glu Glu Leu Gly Met Gln Glu Tyr Ala
            980                 985                 990

Ile Thr Asn Asp Lys Thr Lys Arg Pro Val Ala Leu Arg Thr Lys Thr
        995                 1000                1005

Leu Ala Asp Leu Leu Glu Ser Phe Ile Ala Ala Leu Tyr Thr Asp
    1010            1015                1020

Lys Asp Leu Glu Tyr Val His Thr Phe Met Asn Val Cys Phe Phe
    1025            1030                1035

Pro Arg Leu Lys Glu Phe Ile Leu Asn Gln Asp Trp Asn Asp Pro
    1040            1045                1050

Lys Ser Gln Leu Gln Gln Cys Cys Leu Thr Leu Arg Thr Glu Gly
    1055            1060                1065

Lys Glu Pro Asp Ile Pro Leu Tyr Lys Thr Leu Gln Thr Val Gly
    1070            1075                1080

Pro Ser His Ala Arg Thr Tyr Thr Val Ala Val Tyr Phe Lys Gly
    1085            1090                1095

Glu Arg Ile Gly Cys Gly Lys Gly Pro Ser Ile Gln Gln Ala Glu
    1100            1105                1110

Met Gly Ala Ala Met Asp Ala Leu Glu Lys Tyr Asn Phe Pro Gln
    1115            1120                1125

Met Ala His Gln Lys Arg Phe Ile Glu Arg Lys Tyr Arg Gln Glu
    1130            1135                1140

Leu Lys Glu Met Arg Trp Glu Arg Glu His Gln Glu Arg Glu Pro
    1145            1150                1155

Asp Glu Thr Glu Asp Ile Lys Lys
    1160            1165

<210> SEQ ID NO 15
<211> LENGTH: 1923
<212> TYPE: DNA
<213> ORGANISM: Artificial Sequence
<220> FEATURE:
<223> OTHER INFORMATION: VSV-G H2A Chimeric Protein with VSV-G at the
      N-terminal Nucleotide Sequence
<220> FEATURE:
<221> NAME/KEY: misc_feature
<222> LOCATION: (1)..(1923)

<400> SEQUENCE: 15
atgaagtgcc ttttgtactt agcttttttta ttcatcgggg tgaattgcaa gttcaccata      60 gttttttccac acaaccaaaa aggaaactgg aaaaatgttc cttccaatta ccattattgc    120
ccgtcaagct cagatttaaa ttggcataat gacttaatag cacagcctt acaagtcaaa      180 atgcccaaga gtcacaaggc tattcaagca gacggttgga tgtgtcatgc ttccaaatgg    240

```
gtcactactt gtgatttccg ctggtacgga ccgaagtata taacacattc catccgatcc     300
ttcactccat ctgtagaaca atgcaaggaa agcattgaac aaacgaaaca aggaacttgg     360
ctgaatccag gcttccctcc tcaaagttgt ggatatgcaa ctgtgacgga tgctgaagca     420
gcgattgtcc aggtgactcc tcaccatgtg cttgttgatg aatacacagg agaatgggtt     480
gattcacagt tcatcaacgg aaaatgcagc aatgacatat gccccactgt ccataactcc     540
acaacctggc attccgacta taaggtcaaa gggctatgtg attctaacct catttccacg     600
gacatcacct tcttctcaga ggacggagag ctatcatccc taggaaagga gggcacaggg     660
ttcagaagta actactttgc ttatgaaact ggagacaagg cctgcaaaat gcagtactgc     720
aagcattggg gagtcagact cccatcaggt gtctggttcg agatggctga taaggatctc     780
tttgctgcag ccagattccc tgaatgccca aagggtcaa gtatctctgc tccatctcag     840
acctcagtgg atgtaagtct cattcaggac gttgagagga tcttggatta ttccctctgc     900
caagaaacct ggagcaaaat cagagcgggt cttcccatct ctccagtgga tctcagctat     960
cttgctccta aaaacccagg aaccggtcct gtctttacca taatcaatgg taccctaaaa    1020
tactttgaga ccagatacat cagagtcgat attgctgctc caatcctctc aagaatggtc    1080
ggaatgatca gtggaactac cacagaaagg gaactgtggg atgactgggc tccatatgaa    1140
gacgtggaaa ttggacccaa tggagttctg aggaccagtt aggatataa gtttccttta    1200 tatatgattg gacatggtat gttggactcc gatcttcatc ttagctcaaa ggctcaggtg    1260
tttgaacatc ctcacattca agacgctgct tcgcagcttc ctgatgatga gactttattt    1320
tttggtgata ctgggctatc caaaaatcca atcgagtttg tagaaggttg gttcagtagt    1380
tggaagagct ctattgcctc ttttttcttt atcatagggt taatcattgg actattcttg    1440
gttctccgag ttggtatttta tctttgcatt aaattaaagc acaccaagaa aagacagatt    1500
tatacagaca tagagatgaa ccgacttgga agtctggac gtggaaagca aggcggcaaa    1560
gctcgggcaa aagctaaaac gcgttcttcc agggccggtc ttcagtttcc agttggccgt    1620
gtgcaccgcc tcctccgcaa aggcaactac tccgaacgag tcggggccgg cgctccagtg    1680
tacctggcag cggtgctgga atatctgacg gccgagatct tagagctagc tggcaacgcg    1740
gctcgcgaca ataagaagac ccgcatcatc ccgcgccacc tgcagctagc catccgcaac    1800
gacgaggagc taaataagct tctaggtcgc gtgaccatcg cgcagggcgg tgtcctgccc    1860
aacatccagg ccgtattgct gcctaagaag acggagagcc accataaggc caagggcaag    1920
tga                                                                  1923
```

<210> SEQ ID NO 16
<211> LENGTH: 640
<212> TYPE: PRT
<213> ORGANISM: Artificial Sequence
<220> FEATURE:
<223> OTHER INFORMATION: VSV-G H2A Chimeric Protein with VSV-G at the
      N-terminal Amino Acid Sequence
<220> FEATURE:
<221> NAME/KEY: CHAIN
<222> LOCATION: (1)..(640)

<400> SEQUENCE: 16

Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

-continued

```
Val Pro Ser Asn Tyr His Tyr Cys Pro Ser Ser Ser Asp Leu Asn Trp
             35                  40                  45
His Asn Asp Leu Ile Gly Thr Ala Leu Gln Val Lys Met Pro Lys Ser
 50                  55                  60
His Lys Ala Ile Gln Ala Asp Gly Trp Met Cys His Ala Ser Lys Trp
 65                  70                  75                  80
Val Thr Thr Cys Asp Phe Arg Trp Tyr Gly Pro Lys Tyr Ile Thr His
                 85                  90                  95
Ser Ile Arg Ser Phe Thr Pro Ser Val Glu Gln Cys Lys Glu Ser Ile
             100                 105                 110
Glu Gln Thr Lys Gln Gly Thr Trp Leu Asn Pro Gly Phe Pro Pro Gln
             115                 120                 125
Ser Cys Gly Tyr Ala Thr Val Thr Asp Ala Glu Ala Ile Val Gln
         130                 135                 140
Val Thr Pro His His Val Leu Val Asp Glu Tyr Thr Gly Glu Trp Val
145                 150                 155                 160
Asp Ser Gln Phe Ile Asn Gly Lys Cys Ser Asn Asp Ile Cys Pro Thr
                 165                 170                 175
Val His Asn Ser Thr Thr Trp His Ser Asp Tyr Lys Val Lys Gly Leu
             180                 185                 190
Cys Asp Ser Asn Leu Ile Ser Thr Asp Ile Thr Phe Phe Ser Glu Asp
         195                 200                 205
Gly Glu Leu Ser Ser Leu Gly Lys Glu Gly Thr Gly Phe Arg Ser Asn
    210                 215                 220
Tyr Phe Ala Tyr Glu Thr Gly Asp Lys Ala Cys Lys Met Gln Tyr Cys
225                 230                 235                 240
Lys His Trp Gly Val Arg Leu Pro Ser Gly Val Trp Phe Glu Met Ala
                 245                 250                 255
Asp Lys Asp Leu Phe Ala Ala Ala Arg Phe Pro Glu Cys Pro Glu Gly
             260                 265                 270
Ser Ser Ile Ser Ala Pro Ser Gln Thr Ser Val Asp Val Ser Leu Ile
         275                 280                 285
Gln Asp Val Glu Arg Ile Leu Asp Tyr Ser Leu Cys Gln Glu Thr Trp
    290                 295                 300
Ser Lys Ile Arg Ala Gly Leu Pro Ile Ser Pro Val Asp Leu Ser Tyr
305                 310                 315                 320
Leu Ala Pro Lys Asn Pro Gly Thr Gly Pro Val Phe Thr Ile Ile Asn
                 325                 330                 335
Gly Thr Leu Lys Tyr Phe Glu Thr Arg Tyr Ile Arg Val Asp Ile Ala
             340                 345                 350
Ala Pro Ile Leu Ser Arg Met Val Gly Met Ile Ser Gly Thr Thr Thr
         355                 360                 365
Glu Arg Glu Leu Trp Asp Asp Trp Ala Pro Tyr Glu Asp Val Glu Ile
    370                 375                 380
Gly Pro Asn Gly Val Leu Arg Thr Ser Leu Gly Tyr Lys Phe Pro Leu
385                 390                 395                 400
Tyr Met Ile Gly His Gly Met Leu Asp Ser Asp Leu His Leu Ser Ser
                 405                 410                 415
Lys Ala Gln Val Phe Glu His Pro His Ile Gln Asp Ala Ala Ser Gln
             420                 425                 430
Leu Pro Asp Asp Glu Thr Leu Phe Phe Gly Asp Thr Gly Leu Ser Lys
         435                 440                 445
Asn Pro Ile Glu Phe Val Glu Gly Trp Phe Ser Ser Trp Lys Ser Ser
```

```
                450             455             460
Ile Ala Ser Phe Phe Phe Ile Ile Gly Leu Ile Ile Gly Leu Phe Leu
465                 470                 475                 480

Val Leu Arg Val Gly Ile Tyr Leu Cys Ile Lys Leu Lys His Thr Lys
                485                 490                 495

Lys Arg Gln Ile Tyr Thr Asp Ile Glu Met Asn Arg Leu Gly Lys Ser
                500                 505                 510

Gly Arg Gly Lys Gln Gly Gly Lys Ala Arg Ala Lys Ala Lys Thr Arg
                515                 520                 525

Ser Ser Arg Ala Gly Leu Gln Phe Pro Val Gly Arg Val His Arg Leu
                530                 535                 540

Leu Arg Lys Gly Asn Tyr Ser Glu Arg Val Gly Ala Gly Ala Pro Val
545                 550                 555                 560

Tyr Leu Ala Ala Val Leu Glu Tyr Leu Thr Ala Glu Ile Leu Glu Leu
                565                 570                 575

Ala Gly Asn Ala Ala Arg Asp Asn Lys Lys Thr Arg Ile Ile Pro Arg
                580                 585                 590

His Leu Gln Leu Ala Ile Arg Asn Asp Glu Glu Leu Asn Lys Leu Leu
                595                 600                 605

Gly Arg Val Thr Ile Ala Gln Gly Gly Val Leu Pro Asn Ile Gln Ala
610                 615                 620

Val Leu Leu Pro Lys Lys Thr Glu Ser His His Lys Ala Lys Gly Lys
625                 630                 635                 640

<210> SEQ ID NO 17
<211> LENGTH: 1911
<212> TYPE: DNA
<213> ORGANISM: Artificial Sequence
<220> FEATURE:
<223> OTHER INFORMATION: VSV-G H2B Chimeric Protein with VSV-G at the
      N-terminal Nucleotide Sequence
<220> FEATURE:
<221> NAME/KEY: misc_feature
<222> LOCATION: (1)..(1911)

<400> SEQUENCE: 17
atgaagtgcc ttttgtactt agcttttttta ttcatcgggg tgaattgcaa gttcaccata      60
gtttttccac acaaccaaaa aggaaactgg aaaaatgttc cttccaatta ccattattgc     120
ccgtcaagct cagatttaaa ttggcataat gacttaatag cacagcctt acaagtcaaa      180 atgcccaaga gtcacaaggc tattcaagca gacggttgga tgtgtcatgc ttccaaatgg     240
gtcactactt gtgatttccg ctggtacgga ccgaagtata taacacattc catccgatcc     300
ttcactccat ctgtagaaca atgcaaggaa agcattgaac aaacgaaaca aggaacttgg     360
ctgaatccag gcttccctcc tcaaagttgt ggatatgcaa ctgtgacgga tgctgaagca     420
gcgattgtcc aggtgactcc tcaccatgtg cttgttgatg aatacacagg agaatgggtt     480
gattcacagt tcatcaacgg aaaatgcagc aatgacatat gccccactgt ccataactcc     540
acaacctggc attccgacta taaggtcaaa gggctatgtg attctaacct catttccacg     600
gacatcacct tcttctcaga ggacggagag ctatcatccc taggaaagga gggcacaggg     660
ttcagaagta actactttgc ttatgaaact ggagacaagg cctgcaaaat gcagtactgc     720
aagcattggg gagtcagact cccatcaggt gtctggttcg agatggctga taaggatctc     780
tttgctgcag ccagattccc tgaatgccca gaagggtcaa gtatctctgc tccatctcag     840
acctcagtgg atgtaagtct cattcaggac gttgagagga tcttggatta ttccctctgc     900
```

```
caagaaacct ggagcaaaat cagagcgggt cttcccatct ctccagtgga tctcagctat   960
cttgctccta aaaacccagg aaccggtcct gtctttacca taatcaatgg taccctaaaa  1020
tactttgaga ccagatacat cagagtcgat attgctgctc caatcctctc aagaatggtc  1080
ggaatgatca gtggaactac cacagaaagg gaactgtggg atgactgggc tccatatgaa  1140
gacgtggaaa ttggacccaa tggagttctg aggaccagtt taggatataa gtttccttta  1200
tatatgattg acatggtat gttggactcc gatcttcatc ttagctcaaa ggctcaggtg  1260
tttgaacatc ctcacattca agacgctgct tcgcagcttc ctgatgatga actttatttt  1320
tttggtgata ctgggctatc caaaaatcca atcgagtttg tagaaggttg gttcagtagt  1380
tggaagagct ctattgcctc ttttttcttt atcataggg taatcattgg actattcttg  1440
gttctccgag ttggtatttta tctttgcatt aaattaaagc acaccaagaa aagacagatt  1500
tatacagaca tagagatgaa ccgacttgga aagccagacc cgtccaaatc ggctcctgcg  1560
cccaagaagg gttctaaaaa ggctgtcacc aaggcacaga gaaggacgg caagaagcgc  1620
aagcgcggcc gcaaggagag ctattctatc tacgtgtaca aggtgctgaa gcaggtgcac  1680
cccgacaccg gcatctcgtc caaggccatg gcatcatga actccttcgt caatgacatc  1740
ttcgagcgca tcgccagcga ggcctcccgc ctggcacact acaacaagcg ctccaccatc  1800
acgtcccgcg aagtgcagac ggccgttcgc ctgctgctgc ccggcgagct ggccaagcac  1860
gccgtgtccg agggcaccaa ggctgtcacc aagtacacca gctccaagtg a            1911
```

<210> SEQ ID NO 18
<211> LENGTH: 636
<212> TYPE: PRT
<213> ORGANISM: Artificial Sequence
<220> FEATURE:
<223> OTHER INFORMATION: VSV-G H2B Chimeric Protein with VSV-G at the
      N-terminal Amino Acid Sequence
<220> FEATURE:
<221> NAME/KEY: CHAIN
<222> LOCATION: (1)..(636)

<400> SEQUENCE: 18

```
Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Ala Leu Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr His
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Ala Ile Val Gln
    130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Asp Ile Cys Pro Thr
```

```
              165                 170                 175
Val His Asn Ser Thr Thr Trp His Ser Asp Tyr Lys Val Lys Gly Leu
            180                 185                 190

Cys Asp Ser Asn Leu Ile Ser Thr Asp Ile Thr Phe Ser Glu Asp
            195                 200             205

Gly Glu Leu Ser Ser Leu Gly Lys Glu Gly Thr Gly Phe Arg Ser Asn
        210                 215                 220

Tyr Phe Ala Tyr Glu Thr Gly Asp Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Arg Phe Pro Glu Cys Pro Glu Gly
                260                 265                 270

Ser Ser Ile Ser Ala Pro Ser Gln Thr Ser Val Asp Val Ser Leu Ile
            275                 280                 285

Gln Asp Val Glu Arg Ile Leu Asp Tyr Ser Leu Cys Gln Glu Thr Trp
        290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Val Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
                355                 360                 365

Glu Arg Glu Leu Trp Asp Asp Trp Ala Pro Tyr Glu Asp Val Glu Ile
        370                 375                 380

Gly Pro Asn Gly Val Leu Arg Thr Ser Leu Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Thr Leu Phe Phe Gly Asp Thr Gly Leu Ser Lys
        435                 440                 445

Asn Pro Ile Glu Phe Val Glu Gly Trp Phe Ser Ser Trp Lys Ser Ser
        450                 455                 460

Ile Ala Ser Phe Phe Phe Ile Ile Gly Leu Ile Ile Gly Leu Phe Leu
465                 470                 475                 480

Val Leu Arg Val Gly Ile Tyr Leu Cys Ile Lys Leu Lys His Thr Lys
                485                 490                 495

Lys Arg Gln Ile Tyr Thr Asp Ile Glu Met Asn Arg Leu Gly Lys Pro
            500                 505                 510

Asp Pro Ser Lys Ser Ala Pro Ala Pro Lys Lys Gly Ser Lys Lys Ala
            515                 520                 525

Val Thr Lys Ala Gln Lys Lys Asp Gly Lys Lys Arg Lys Arg Gly Arg
        530                 535                 540

Lys Glu Ser Tyr Ser Ile Tyr Val Tyr Lys Val Leu Lys Gln Val His
545                 550                 555                 560

Pro Asp Thr Gly Ile Ser Ser Lys Ala Met Gly Ile Met Asn Ser Phe
                565                 570                 575

Val Asn Asp Ile Phe Glu Arg Ile Ala Ser Glu Ala Ser Arg Leu Ala
                580                 585                 590
```

His Tyr Asn Lys Arg Ser Thr Ile Thr Ser Arg Glu Val Gln Thr Ala
        595                 600                 605

Val Arg Leu Leu Leu Pro Gly Glu Leu Ala Lys His Ala Val Ser Glu
    610                 615                 620

Gly Thr Lys Ala Val Thr Lys Tyr Thr Ser Ser Lys
625                 630                 635

<210> SEQ ID NO 19
<211> LENGTH: 1938
<212> TYPE: DNA
<213> ORGANISM: Artificial Sequence
<220> FEATURE:
<223> OTHER INFORMATION: VSV-G H3 Chimeric Protein with VSV-G at the
      N-terminal Nucleotide Sequence
<220> FEATURE:
<221> NAME/KEY: misc_feature
<222> LOCATION: (1)..(1938)

<400> SEQUENCE: 19

| | | | | | |
|---|---|---|---|---|---|
| atgaagtgcc | ttttgtactt | agcttttta | ttcatcgggg | tgaattgcaa | gttcaccata | 60 |
| gttttccac | acaaccaaaa | aggaaactgg | aaaaatgttc | cttccaatta | ccattattgc | 120 |
| ccgtcaagct | cagatttaaa | ttggcataat | gacttaatag | gcacagcctt | acaagtcaaa | 180 |
| atgcccaaga | gtcacaaggc | tattcaagca | gacggttgga | tgtgtcatgc | ttccaaatgg | 240 |
| gtcactactt | gtgatttccg | ctggtacgga | ccgaagtata | taacacattc | catccgatcc | 300 |
| ttcactccat | ctgtagaaca | atgcaaggaa | agcattgaac | aaacgaaaca | aggaacttgg | 360 |
| ctgaatccag | gcttccctcc | tcaaagttgt | ggatatgcaa | ctgtgacgga | tgctgaagca | 420 |
| gcgattgtcc | aggtgactcc | tcaccatgtg | cttgttgatg | aatacacagg | agaatgggtt | 480 |
| gattcacagt | tcatcaacgg | aaaatgcagc | aatgacatat | gccccactgt | ccataactcc | 540 |
| acaacctggc | attccgacta | taaggtcaaa | gggctatgtg | attctaacct | catttccacg | 600 |
| gacatcacct | tcttctcaga | ggacggagag | ctatcatccc | taggaaagga | gggcacaggg | 660 |
| ttcagaagta | actactttgc | ttatgaaact | ggagacaagg | cctgcaaaat | gcagtactgc | 720 |
| aagcattggg | gagtcagact | cccatcaggt | gtctggttcg | agatggctga | taaggatctc | 780 |
| tttgctgcag | ccagattccc | tgaatgccca | gaagggcaa | gtatctctgc | tccatctcag | 840 |
| acctcagtgg | atgtaagtct | cattcaggac | gttgagagga | tcttggatta | ttccctctgc | 900 |
| caagaaacct | ggagcaaaat | cagagcgggt | cttcccatct | ctccagtgga | tctcagctat | 960 |
| cttgctccta | aaacccagg | aaccggtcct | gtctttacca | taatcaatgg | taccctaaaa | 1020 |
| tactttgaga | ccagatacat | cagagtcgat | attgctgctc | caatcctctc | aagaatggtc | 1080 |
| ggaatgatca | gtggaactac | cacagaaagg | gaactgtggg | atgactgggc | tccatatgaa | 1140 |
| gacgtggaaa | ttggacccaa | tggagttctg | aggaccagtt | taggatataa | gtttcctta | 1200 |
| tatatgattg | acatggtat | gttggactcc | gatcttcatc | ttagctcaaa | ggctcaggtg | 1260 |
| tttgaacatc | ctcacattca | agacgctgct | tcgcagcttc | ctgatgatga | actttattt | 1320 |
| tttggtgata | ctgggctatc | caaaaatcca | atcgagtttg | tagaaggttg | gttcagtagt | 1380 |
| tggaagagct | ctattgcctc | tttttctt | atcatagggt | taatcattgg | actattcttg | 1440 |
| gttctccgag | ttggtattta | tctttgcatt | aaattaaagc | acaccaagaa | aagacagatt | 1500 |
| tatacagaca | tagagatgaa | ccgacttgga | aaggcccgaa | ccaagcagac | tgctcgtaaa | 1560 |
| tccaccggtg | ggaagccccc | cgcaaacag | ctggccacga | agctgccag | gaaaagcacc | 1620 |
| ccctctacct | gcggggtgaa | gcctcatcgc | tacaggcctg | ggaccgtggc | gcttcgagag | 1680 |

```
attcgtcgtt atcagaagtc gaccgagctg ctcatccgga agctgcccct tccagaggttg    1740 gtgagggaga tcgcgcagga tttcaacact gacctgaggt ttcagagcgc agccgtcggt    1800
gcgctgcagg aggctagcga agcgtacctg gtgggtctgt tggaagatac taacctgtgt    1860
gccatccacg ctaagagagt caccatcatg cccaaagaca tccagttggc tcgccggata    1920
cggggagaga gagcttaa                                                   1938
```

<210> SEQ ID NO 20
<211> LENGTH: 645
<212> TYPE: PRT
<213> ORGANISM: Artificial Sequence
<220> FEATURE:
<223> OTHER INFORMATION: VSV-G H3 Chimeric Protein with VSV-G at the
      N-terminal Amino Acid Sequence
<220> FEATURE:
<221> NAME/KEY: CHAIN
<222> LOCATION: (1)..(645)

<400> SEQUENCE: 20

```
Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Ala Leu Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr His
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Ala Ile Val Gln
    130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Asp Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Thr Asp Ile Thr Phe Phe Ser Glu Asp
        195                 200                 205

Gly Glu Leu Ser Ser Leu Gly Lys Glu Gly Thr Gly Phe Arg Ser Asn
    210                 215                 220

Tyr Phe Ala Tyr Glu Thr Gly Asp Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285
```

```
Gln Asp Val Glu Arg Ile Leu Asp Tyr Ser Leu Cys Gln Glu Thr Trp
290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Val Phe Thr Ile Ile Asn
                325                 330                 335

Gly Thr Leu Lys Tyr Phe Glu Thr Arg Tyr Ile Arg Val Asp Ile Ala
                340                 345                 350

Ala Pro Ile Leu Ser Arg Met Val Gly Met Ile Ser Gly Thr Thr Thr
                355                 360                 365

Glu Arg Glu Leu Trp Asp Asp Trp Ala Pro Tyr Glu Asp Val Glu Ile
370                 375                 380

Gly Pro Asn Gly Val Leu Arg Thr Ser Leu Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
                420                 425                 430

Leu Pro Asp Asp Glu Thr Leu Phe Phe Gly Asp Thr Gly Leu Ser Lys
                435                 440                 445

Asn Pro Ile Glu Phe Val Glu Gly Trp Phe Ser Ser Trp Lys Ser Ser
450                 455                 460

Ile Ala Ser Phe Phe Phe Ile Ile Gly Leu Ile Ile Gly Leu Phe Leu
465                 470                 475                 480

Val Leu Arg Val Gly Ile Tyr Leu Cys Ile Lys Leu Lys His Thr Lys
                485                 490                 495

Lys Arg Gln Ile Tyr Thr Asp Ile Glu Met Asn Arg Leu Gly Lys Ala
                500                 505                 510

Arg Thr Lys Gln Thr Ala Arg Lys Ser Thr Gly Gly Lys Ala Pro Arg
                515                 520                 525

Lys Gln Leu Ala Thr Lys Ala Ala Arg Lys Ser Thr Pro Ser Thr Cys
530                 535                 540

Gly Val Lys Pro His Arg Tyr Arg Pro Gly Thr Val Ala Leu Arg Glu
545                 550                 555                 560

Ile Arg Arg Tyr Gln Lys Ser Thr Glu Leu Leu Ile Arg Lys Leu Pro
                565                 570                 575

Phe Gln Arg Leu Val Arg Glu Ile Ala Gln Asp Phe Asn Thr Asp Leu
                580                 585                 590

Arg Phe Gln Ser Ala Ala Val Gly Ala Leu Gln Glu Ala Ser Glu Ala
                595                 600                 605

Tyr Leu Val Gly Leu Leu Glu Asp Thr Asn Leu Cys Ala Ile His Ala
610                 615                 620

Lys Arg Val Thr Ile Met Pro Lys Asp Ile Gln Leu Ala Arg Arg Ile
625                 630                 635                 640

Arg Gly Glu Arg Ala
            645

<210> SEQ ID NO 21
<211> LENGTH: 1842
<212> TYPE: DNA
<213> ORGANISM: Artificial Sequence
<220> FEATURE:
<223> OTHER INFORMATION: VSV-G H4 Chimeric Protein with VSV-G at the
      N-terminal Nucleotide Sequence
<220> FEATURE:
<221> NAME/KEY: misc_feature
```

<222> LOCATION: (1)..(1842)

<400> SEQUENCE: 21

```
atgaagtgcc ttttgtactt agctttttta ttcatcgggg tgaattgcaa gttcaccata      60
gtttttccac acaaccaaaa aggaaactgg aaaaatgttc cttccaatta ccattattgc     120
ccgtcaagct cagatttaaa ttggcataat gacttaatag gcacagcctt acaagtcaaa     180
atgcccaaga gtcacaaggc tattcaagca gacggttgga tgtgtcatgc ttccaaatgg     240
gtcactactt gtgatttccg ctggtacgga ccgaagtata acacattc  catccgatcc     300
ttcactccat ctgtagaaca atgcaaggaa agcattgaac aaacgaaaca aggaacttgg     360
ctgaatccag gcttccctcc tcaaagttgt ggatatgcaa ctgtgacgga tgctgaagca     420
gcgattgtcc aggtgactcc tcaccatgtg cttgttgatg aatacacagg agaatgggtt     480
gattcacagt tcatcaacgg aaaatgcagc aatgacatat gccccactgt ccataactcc     540
acaacctggc attccgacta taaggtcaaa gggctatgtg attctaacct catttccacg     600
gacatcacct tcttctcaga ggacggagag ctatcatccc taggaaagga gggcacaggg     660
ttcagaagta actactttgc ttatgaaact ggagacaagg cctgcaaaat gcagtactgc     720
aagcattggg gagtcagact cccatcaggt gtctggttcg agatggctga taaggatctc     780
tttgctgcag ccagattccc tgaatgccca gaagggtcaa gtatctctgc tccatctcag     840
acctcagtga tgtaagtct cattcaggac gttgagagga tcttggatta ttccctctgc     900
caagaaacct ggagcaaaat cagagcgggt cttcccatct ctccagtgga tctcagctat     960
cttgctccta aaaacccagg aaccggtcct gtctttacca taatcaatgg tacccctaaaa    1020
tactttgaga ccagatacat cagagtcgat attgctgctc caatcctctc aagaatggtc    1080
ggaatgatca gtggaactac cacagaaagg gaactgtggg atgactgggc tccatatgaa    1140
gacgtggaaa ttggacccaa tggagttctg aggaccagtt aggatataa gtttccttta    1200
tatatgattg acatggtat gttggactcc gatcttcatc ttagctcaaa ggctcaggtg    1260
tttgaacatc ctcacattca agacgctgct tcgcagcttc ctgatgatga actttatttt    1320
tttggtgata ctgggctatc caaaaatcca atcgagtttg tagaaggttg gttcagtagt    1380
tggaagagct ctattgcctc ttttttcttt atcatagggt taatcattgg actattcttg    1440
gttctccgag ttggtattta tctttgcatt aaattaaagc acaccaagaa aagacagatt    1500
tatacagaca tagagatgaa ccgacttgga aagtctggtc gcggcaaagg cggtaaaggt    1560
ttgggtaagg gaggtgccaa gcgtcaccga aaagtgctgc gggataacat ccaaggcatc    1620
accaaaccgg ccattcggcg ccttgctagg cgtggtgggg ttaagcgaat tccggtttg    1680
atttatgagg agactcgtgg cgttctcaag gtgtttctgg agaacgtgat ccggacgcc    1740
gtgacctaca cggagcacgc caagcgcaag actgtcactg ccatggatgt ggtttacgcg    1800
ctcaagcgtc aaggacgcac tctgtacggc ttcggcggtt aa                      1842
```

<210> SEQ ID NO 22
<211> LENGTH: 613
<212> TYPE: PRT
<213> ORGANISM: Artificial Sequence
<220> FEATURE:
<223> OTHER INFORMATION: VSV-G H4 Chimeric Protein with VSV-G at the
N-terminal Amino Acid Sequence
<220> FEATURE:
<221> NAME/KEY: CHAIN
<222> LOCATION: (1)..(613)

<400> SEQUENCE: 22

```
Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Asp Leu Asn Trp
        35                  40                  45

His Asn Asp Leu Ile Gly Thr Ala Leu Gln Val Lys Met Pro Lys Ser
65                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr His
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
            115                 120                 125

Ser Cys Gly Tyr Ala Thr Val Thr Asp Ala Glu Ala Ile Val Gln
    130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Asp Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Thr Asp Ile Thr Phe Phe Ser Glu Asp
            195                 200                 205

Gly Glu Leu Ser Ser Leu Gly Lys Glu Gly Thr Gly Phe Arg Ser Asn
210                 215                 220

Tyr Phe Ala Tyr Glu Thr Gly Asp Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Arg Phe Pro Glu Cys Pro Glu Gly
            260                 265                 270

Ser Ser Ile Ser Ala Pro Ser Gln Thr Ser Val Asp Val Ser Leu Ile
            275                 280                 285

Gln Asp Val Glu Arg Ile Leu Asp Tyr Ser Leu Cys Gln Glu Thr Trp
    290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Val Phe Thr Ile Ile Asn
            325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
            355                 360                 365

Glu Arg Glu Leu Trp Asp Asp Trp Ala Pro Tyr Glu Asp Val Glu Ile
            370                 375                 380

Gly Pro Asn Gly Val Leu Arg Thr Ser Leu Gly Tyr Lys Phe Pro Leu
385                 390                 395                 400

Tyr Met Ile Gly His Gly Met Leu Asp Ser Asp Leu His Leu Ser Ser
                405                 410                 415
```

-continued

```
Lys Ala Gln Val Phe Glu His Pro His Ile Gln Asp Ala Ala Ser Gln
                420                 425                 430
Leu Pro Asp Asp Glu Thr Leu Phe Phe Gly Asp Thr Gly Leu Ser Lys
            435                 440                 445
Asn Pro Ile Glu Phe Val Glu Gly Trp Phe Ser Ser Trp Lys Ser Ser
        450                 455                 460
Ile Ala Ser Phe Phe Phe Ile Ile Gly Leu Ile Ile Gly Leu Phe Leu
465                 470                 475                 480
Val Leu Arg Val Gly Ile Tyr Leu Cys Ile Lys Leu Lys His Thr Lys
                485                 490                 495
Lys Arg Gln Ile Tyr Thr Asp Ile Glu Met Asn Arg Leu Gly Lys Ser
                500                 505                 510
Gly Arg Gly Lys Gly Lys Gly Leu Gly Lys Gly Gly Ala Lys Arg
            515                 520                 525
His Arg Lys Val Leu Arg Asp Asn Ile Gln Gly Ile Thr Lys Pro Ala
        530                 535                 540
Ile Arg Arg Leu Ala Arg Arg Gly Gly Val Lys Arg Ile Ser Gly Leu
545                 550                 555                 560
Ile Tyr Glu Glu Thr Arg Gly Val Leu Lys Val Phe Leu Glu Asn Val
                565                 570                 575
Ile Arg Asp Ala Val Thr Tyr Thr Glu His Ala Lys Arg Lys Thr Val
                580                 585                 590
Thr Ala Met Asp Val Val Tyr Ala Leu Lys Arg Gln Gly Arg Thr Leu
            595                 600                 605
Tyr Gly Phe Gly Gly
        610
```

<210> SEQ ID NO 23
<211> LENGTH: 1977
<212> TYPE: DNA
<213> ORGANISM: Artificial Sequence
<220> FEATURE:
<223> OTHER INFORMATION: VSV-G SSBP-1 Chimeric Protein with VSV-G at the
      N-terminal Nucleotide Sequence
<220> FEATURE:
<221> NAME/KEY: misc_feature
<222> LOCATION: (1)..(1977)

<400> SEQUENCE: 23

```
atgaagtgcc ttttgtactt agctttttta ttcatcgggg tgaattgcaa gttcaccata      60
gttttttccac acaaccaaaa aggaaactgg aaaaatgttc cttccaatta ccattattgc    120
ccgtcaagct cagatttaaa ttggcataat gacttaatag cacagcctt acaagtcaaa      180
atgcccaaga gtcacaaggc tattcaagca gacggttgga tgtgtcatgc ttccaaatgg     240
gtcactactt tgtgatttccg ctggtacgga ccgaagtata acacattc catccgatcc      300
ttcactccat ctgtagaaca atgcaaggaa agcattgaac aaacgaaaca aggaacttgg     360
ctgaatccag cttccctcc tcaaagttgt ggatatgcaa ctgtgacgga tgctgaagca     420
gcgattgtcc aggtgactcc tcaccatgtg cttgttgatg aatacacagg agaatgggtt     480
gattcacagt tcatcaacgg aaaatgcagc aatgacatat gccccactgt ccataactcc    540
acaacctggc attccgacta taaggtcaaa gggctatgtg attctaacct catttccacg    600
gacatcacct tcttctcaga ggacggagag ctatcatccc taggaaagga gggcacaggg    660
ttcagaagta actactttgc ttatgaaact ggagacaagg cctgcaaaat gcagtactgc    720
aagcattggg gagtcagact cccatcaggt gtctggttcg agatggctga taaggatctc    780
```

-continued

```
tttgctgcag ccagattccc tgaatgccca gaagggtcaa gtatctctgc tccatctcag    840
acctcagtgg atgtaagtct cattcaggac gttgagagga tcttggatta ttccctctgc    900
caagaaacct ggagcaaaat cagagcgggt cttcccatct ctccagtgga tctcagctat    960
cttgctccta aaacccagg aaccggtcct gtctttacca taatcaatgg tacccctaaaa    1020 tactttgaga ccagatacat cagagtcgat attgctgctc caatcctctc aagaatggtc    1080
ggaatgatca gtggaactac cacagaaagg gaactgtggg atgactgggc tccatatgaa    1140
gacgtggaaa ttggacccaa tggagttctg aggaccagtt taggatataa gtttcctta    1200 tatatgattg acatggtat gttggactcc gatcttcatc ttagctcaaa ggctcaggtg    1260
tttgaacatc ctcacattca agacgctgct tcgcagcttc ctgatgatga actttatt    1320 tttggtgata ctgggctatc caaaaatcca atcgagtttg tagaaggttg gttcagtagt    1380
tggaagagct ctattgcctc tttttctttt atcatagggt taatcattgg actattcttg    1440
gttctccgag ttggtattta tctttgcatt aaattaaagc acaccaagaa agacacagatt   1500 tatacagaca tagagatgaa ccgacttgga aagtttcgaa gacctgtatt acaggtactt    1560 cgtcagttg taagacatga gtccgaaaca actaccagtt tggttcttga agatccctg    1620 aatcgtgtgc acttacttgg gcgagtgggt caggaccctg tcttgagaca ggtggaagga    1680
aaaaatccag tcacaatatt ttctctagca actaatgaga tgtggcgatc aggggatagt    1740
gaagtttacc aactgggtga tgtcagtcaa agacaacat ggcacagaat atcagtattc    1800
cggccaggcc tcagagacgt ggcatatcaa tatgtgaaaa aggggtctcg aatttatttg    1860
gaagggaaaa tagactatgg tgaatacatg gataaaaata atgtgaggcg acaagcaaca    1920
acaatcatag ctgataatat tatatttctg agtgaccaga cgaaagagaa ggagtag       1977
```

<210> SEQ ID NO 24
<211> LENGTH: 658
<212> TYPE: PRT
<213> ORGANISM: Artificial Sequence
<220> FEATURE:
<223> OTHER INFORMATION: VSV-G SSBP-1 Chimeric Protein with VSV-G at the
      N-terminal Amino Acid Sequence
<220> FEATURE:
<221> NAME/KEY: CHAIN
<222> LOCATION: (1)..(658)

<400> SEQUENCE: 24

```
Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Ala Leu Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr His
            85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Ala Ile Val Gln
```

-continued

```
            130                 135                 140
Val Thr Pro His His Val Leu Val Asp Glu Tyr Thr Gly Glu Trp Val
145                 150                 155                 160

Asp Ser Gln Phe Ile Asn Gly Lys Cys Ser Asn Asp Ile Cys Pro Thr
                165                 170                 175

Val His Asn Ser Thr Thr Trp His Ser Asp Tyr Lys Val Lys Gly Leu
                180                 185                 190

Cys Asp Ser Asn Leu Ile Ser Thr Asp Ile Thr Phe Phe Ser Glu Asp
                195                 200                 205

Gly Glu Leu Ser Ser Leu Gly Lys Glu Gly Thr Gly Phe Arg Ser Asn
                210                 215                 220

Tyr Phe Ala Tyr Glu Thr Gly Asp Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
                260                 265                 270

Ser Ser Ile Ser Ala Pro Ser Gln Thr Ser Val Asp Val Ser Leu Ile
                275                 280                 285

Gln Asp Val Glu Arg Ile Leu Asp Tyr Ser Leu Cys Gln Glu Thr Trp
                290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Val Phe Thr Ile Ile Asn
                325                 330                 335

Gly Thr Leu Lys Tyr Phe Glu Thr Arg Tyr Ile Arg Val Asp Ile Ala
                340                 345                 350

Ala Pro Ile Leu Ser Arg Met Val Gly Met Ile Ser Gly Thr Thr Thr
                355                 360                 365

Glu Arg Glu Leu Trp Asp Asp Trp Ala Pro Tyr Glu Asp Val Glu Ile
                370                 375                 380

Gly Pro Asn Gly Val Leu Arg Thr Ser Leu Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
                420                 425                 430

Leu Pro Asp Asp Glu Thr Leu Phe Phe Gly Asp Thr Gly Leu Ser Lys
                435                 440                 445

Asn Pro Ile Glu Phe Val Glu Gly Trp Phe Ser Ser Trp Lys Ser Ser
450                 455                 460

Ile Ala Ser Phe Phe Phe Ile Ile Gly Leu Ile Gly Leu Phe Leu
465                 470                 475                 480

Val Leu Arg Val Gly Ile Tyr Leu Cys Ile Lys Leu Lys His Thr Lys
                485                 490                 495

Lys Arg Gln Ile Tyr Thr Asp Ile Glu Met Asn Arg Leu Gly Lys Phe
                500                 505                 510

Arg Arg Pro Val Leu Gln Val Leu Arg Gln Phe Val Arg His Glu Ser
                515                 520                 525

Glu Thr Thr Thr Ser Leu Val Leu Glu Arg Ser Leu Asn Arg Val His
                530                 535                 540

Leu Leu Gly Arg Val Gly Gln Asp Pro Val Leu Arg Gln Val Glu Gly
545                 550                 555                 560
```

Lys Asn Pro Val Thr Ile Phe Ser Leu Ala Thr Asn Glu Met Trp Arg
                565                 570                 575

Ser Gly Asp Ser Glu Val Tyr Gln Leu Gly Asp Val Ser Gln Lys Thr
            580                 585                 590

Thr Trp His Arg Ile Ser Val Phe Arg Pro Gly Leu Arg Asp Val Ala
        595                 600                 605

Tyr Gln Tyr Val Lys Lys Gly Ser Arg Ile Tyr Leu Glu Gly Lys Ile
    610                 615                 620

Asp Tyr Gly Glu Tyr Met Asp Lys Asn Asn Val Arg Arg Gln Ala Thr
625                 630                 635                 640

Thr Ile Ile Ala Asp Asn Ile Ile Phe Leu Ser Asp Gln Thr Lys Glu
            645                 650                 655

Lys Glu

<210> SEQ ID NO 25
<211> LENGTH: 5655
<212> TYPE: DNA
<213> ORGANISM: Artificial Sequence
<220> FEATURE:
<223> OTHER INFORMATION: RNase III VSV-G Chimeric Protein with VSV-G at
      N-terminal Nucleotide Sequence
<220> FEATURE:
<221> NAME/KEY: misc_feature
<222> LOCATION: (1)..(5655)

<400> SEQUENCE: 25

```
atgaagtgcc ttttgtactt agctttttta ttcatcgggg tgaattgcaa gttcaccata      60
gttttcccac acaaccaaaa aggaaactgg aaaaatgttc cttccaatta ccattattgc     120
ccgtcaagct cagatttaaa ttggcataat gacttaatag cacagcctt acaagtcaaa      180 atgcccaaga gtcacaaggc tattcaagca gacggttgga tgtgtcatgc ttccaaatgg     240
gtcactactt gtgatttccg ctggtacgga ccgaagtata aacacattc catccgatcc      300 ttcactccat ctgtagaaca atgcaaggaa agcattgaac aaacgaaaca aggaacttgg     360
ctgaatccag gcttccctcc tcaaagttgt ggatatgcaa ctgtgacgga tgctgaagca     420
gcgattgtcc aggtgactcc tcaccatgtg cttgttgatg aatacacagg agaatgggtt     480
gattcacagt tcatcaacgg aaaatgcagc aatgacatat gccccactgt ccataactcc     540
acaacctggc attccgacta taaggtcaaa gggctatgtg attctaacct catttccacg     600
gacatcacct tcttctcaga ggacggagag ctatcatccc taggaaagga gggcacaggg     660
ttcagaagta actactttgc ttatgaaact ggagacaagg cctgcaaaat gcagtactgc     720
aagcattggg gagtcagact cccatcaggt gtctggttcg agatggctga taaggatctc     780
tttgctgcag ccagattccc tgaatgccca aagggtcaa gtatctctgc tccatctcag      840
acctcagtgg atgtaagtct cattcaggac gttgagagga tcttggatta ttccctctgc     900
caagaaacct ggagcaaaat cagagcgggt cttcccatct ctccagtgga tctcagctat     960
cttgctccta aaacccagg aaccggtcct gtctttacca aatcaatgg taccctaaaa    1020 tactttgaga ccagatacat cagagtcgat attgctgctc caatcctctc aagaatggtc    1080
ggaatgatca gtggaactac cacagaaagg gaactgtggg atgactgggc tccatatgaa    1140
gacgtggaaa ttggacccaa tggagttctg aggaccagtt aggatataa gtttccttta    1200 tatatgattg acatggtat gttggactcc gatcttcatc ttagctcaaa ggctcaggtg    1260
tttgaacatc ctcacattca agacgctgct tcgcagcttc ctgatgatga acttttattt    1320
```

```
tttggtgata ctgggctatc caaaaatcca atcgagtttg tagaaggttg gttcagtagt    1380
tggaagagct ctattgcctc ttttttcttt atcatagggt taatcattgg actattcttg    1440
gttctccgag ttggtattta tctttgcatt aaattaaagc acaccaagaa aagacagatt    1500
tatacagaca tagagatgaa ccgacttgga aagatgcagg gaaacacatg tcacagaatg    1560
tcgttccacc cgggacgagg gtgtccccga ggacgaggag gacatggagc cagaccctca    1620
gcaccatcct ttaggcccca aaatctgagg ctgcttcacc ctcagcagcc tcctgtgcaa    1680
tatcaatatg aacctccaag tgccccttcc accactttct caaactctcc agccccaat    1740 tttctccctc cacgaccaga ctttgtaccc ttcccccac ccatgcctcc gtcagcgcaa     1800
ggccctcttc cccctgccc aatcaggccg ccttcccca accaccagat gaggcacccc     1860
ttcccagttc ctccttgttt tcctcccatg ccaccaccaa tgccttgtcc taataacccc    1920
ccagtccctg gggcacctcc tggacaaggc actttcccct tcatgatgcc ccctccctcc    1980
atgcctcatc ccccgccccc tccagtcatg ccgcagcagg ttaattatca gtaccctccg    2040
ggctattctc accacaactt cccacctccc agttttaata gtttccagaa caaccctagt    2100
tctttcctgc ccagtgctaa taacagcagt agtcctcatt tcagacatct ccctccatac    2160
ccactcccaa aggctcccag tgagagaagg tccccagaaa ggctgaaaca ctatgatgac    2220
cacaggcacc gagatcacag tcatgggcga ggtgagaggc atcggtccct ggatcggcgg    2280
gagcgaggcc gcagtcccga caggagaaga caagacagcc ggtacagatc tgattatgac    2340
cgagggagaa caccatctcg ccaccgcagc tacgaacgga gcagagagcg agaacgggag    2400
agacacaggc atcgagacaa ccgaagatca ccatctctgg aaaggtccta caaaaaagag    2460
tataagagat ctggaaggag ttacggttta tcggttgttc ctgaacctgc tggatgcaca    2520
ccagaattac ctggggagat tattaaaaat acagattctt gggccccacc cctggagatt    2580
gtgaatcatc gctccccaag tagggagaag aagagagctc gttgggagga agaaaaagac    2640
cgttggagtg acaaccagag ttctggcaaa gacaagaact atacctcaat caaggaaaaa    2700
gagcccgagg agaccatgcc tgacaagaat gaggaggaag aagaagaact tcttaagcct    2760
gtgtggattc gatgcactca ttcagaaaac tactactcca gtgaccccat ggatcaggtg    2820
ggagattcta cagtggttgg aacgagtagg cttcgtgact tatatgacaa atttgaggag    2880
gagttgggga gcaggcaaga aaaggccaaa gctgctcggc ctccgtggga acctccaaag    2940
acgaagctcg atgaagattt agagagttcc agtgaatccg agtgtgagtc tgatgaggac    3000
agcacctgtt ctagcagctc agactctgaa gtttttgacg ttattgcaga atcaaacgc    3060 aaaaaggccc accctgaccg acttcatgat gaactttggt acaacgatcc aggccagatg    3120
aatgatggac cactctgcaa atgcagcgca aaggcaagac gcacaggaat taggcacagc    3180
atttatcctg gagaagaggc catcaagccc tgtcgtccta tgaccaacaa tgctggcaga    3240
cttttccact accggatcac agtctcccg cctacgaact ttttaactga caggccaact     3300
gttatagaat acgatgatca cgagtatatc tttgaaggat tttctatgtt tgcacatgcc    3360
cccctgacca atattccact gtgtaaagta attagattca acatagacta cacgattcat    3420
ttcattgaag atgatgcc ggagaatttt tgtgtgaaag gcttgaact ctttcactg        3480 ttcctattca gagatatttt ggaattatat gactggaatc ttaaaggtcc tttgtttgaa    3540
gacagccctc cctgctgccc aagatttcat ttcatgccac gttttgtaag atttcttcca    3600
gatggaggaa aggaagtgct gtccatgcac cagattctcc tgtacttgtt aaggtgcagc    3660
aaagccctgg tgcctgagga ggagattgcc aatatgcttc agtgggagga gctggagtgg    3720
```

```
cagaaatatg cagaagaatg caaaggcatg attgttacca accctgggac gaaaccaagc    3780
tctgtccgta tcgatcaact ggatcgtgaa cagttcaacc ccgatgtgat tactttccg     3840 attatcgtcc actttgggat acgccctgca cagttgagtt atgcaggaga cccacagtac    3900
caaaaactgt ggaagagtta tgtgaaactt cgccacctcc tagcaaatag tcccaaagtc    3960
aaacaaactg acaaacagaa gctggcacag agggaggaag ccctccaaaa aatacggcag    4020
aagaatacaa tgagacgaga agtaacggtg gagctaagta gccaaggatt ctggaaaact    4080
ggcatccgtt ctgatgtctg tcagcatgca atgatgctac ctgttctgac ccatcatatc    4140
cgctaccacc aatgcctaat gcatttggac aagttgatag gatatacttt ccaagatcgt    4200
tgtctgttgc agctggccat gactcatcca agtcatcatt taaattttgg aatgaatcct    4260
gatcatgcca ggaattcatt atctaactgt ggaattcggc agcccaaata cggagacaga    4320
aaagttcatc acatgcacat gcggaagaaa gggattaaca ccttgataaa tatcatgtca    4380
cgccttggcc aagatgaccc aactccctcg aggattaacc acaatgaacg gttggaattc    4440
ctgggtgatg ctgttgttga atttctgacc agcgtccatt tgtactattt gtttcctagt    4500
ctggaagaag gaggattagc aacctatcgg actgccattg ttcagaatca gcaccttgcc    4560
atgctagcaa agaaacttga actggatcga tttatgctgt atgctcacgg gcctgacctt    4620
tgtagagaat cggaccttcg acatgcaatg gccaattgtt ttgaagcgtt aataggagct    4680
gtttacttgg agggaagcct ggaggaagcc aagcagttat ttggacgctt gctctttaat    4740
gatccggacc tgcgcgaagt ctggctcaat tatcctctcc acccactcca actacaagag    4800
ccaaatactg atcgacaact tattgaaact tctccagttc tacaaaaact tactgagttt    4860
gaagaagcaa ttggagtaat ttttactcat gttcgacttc tggcaagggc attcacattg    4920
agaactgtgg gatttaacca tctgacccta ggccacaatc agagaatgga attcctaggt    4980
gactccataa tgcaactggt agccacagag tacttattca ttcatttccc agatcatcat    5040
gaaggacact taactttgtt gcgaagctct ttggtgaata atagaactca ggccaaggta    5100
gcggaggagc tgggcatgca ggagtacgcc ataaccaacg acaagaccaa gaggcctgtg    5160
gcgcttcgca ccaagacctt ggcggacctt ttggaatcat ttattgcagc gctgtacatt    5220
gataaggatt tggaatatgt tcatactttc atgaatgtct gcttctttcc acgattgaaa    5280
gagttcattt tgaatcagga ttggaatgac cccaaatccc agcttcagca gtgttgcttg    5340
acacttagga cagaaggaaa agagccagac attcctctgt acaagactct gcagacagtg    5400
ggcccatccc atgcccgaac ctacactgtg gctgtttatt tcaagggaga agaataggc     5460 tgtgggaaag gaccaagtat tcagcaagcg gaaatgggag cagcaatgga tgcgcttgaa    5520
aaatataatt ttccccagat ggcccatcag aagcggttca tcgaacggaa gtacagacaa    5580
gagttaaaag aaatgaggtg ggaaagagag catcaagaga gagagccaga tgagactgaa    5640
gacatcaaga aataa                                                     5655
```

<210> SEQ ID NO 26
<211> LENGTH: 1884
<212> TYPE: PRT
<213> ORGANISM: Artificial Sequence
<220> FEATURE:
<223> OTHER INFORMATION: RNase III VSV-G Chimeric Protein with VSV-G at
      N-terminal Amino Acid Sequence
<220> FEATURE:
<221> NAME/KEY: CHAIN
<222> LOCATION: (1)..(1884)

```
<400> SEQUENCE: 26

Met Lys Cys Leu Leu Tyr Leu Ala Phe Leu Phe Ile Gly Val Asn Cys
  1               5                  10                  15

Lys Phe Thr Ile Val Phe Pro His Asn Gln Lys Gly Asn Trp Lys Asn
                 20                  25                  30

Val Pro Ser Asn Tyr His Tyr Cys Pro Ser Ser Asp Leu Asn Trp
             35                  40                  45

His Asn Asp Leu Ile Gly Thr Ala Leu Gln Val Lys Met Pro Lys Ser
 50                  55                  60

His Lys Ala Ile Gln Ala Asp Gly Trp Met Cys His Ala Ser Lys Trp
 65                  70                  75                  80

Val Thr Thr Cys Asp Phe Arg Trp Tyr Gly Pro Lys Tyr Ile Thr His
                 85                  90                  95

Ser Ile Arg Ser Phe Thr Pro Ser Val Glu Gln Cys Lys Glu Ser Ile
                100                 105                 110

Glu Gln Thr Lys Gln Gly Thr Trp Leu Asn Pro Gly Phe Pro Pro Gln
            115                 120                 125

Ser Cys Gly Tyr Ala Thr Val Thr Asp Ala Glu Ala Ile Val Gln
        130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Asp Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Thr Asp Ile Thr Phe Phe Ser Glu Asp
        195                 200                 205

Gly Glu Leu Ser Ser Leu Gly Lys Glu Gly Thr Gly Phe Arg Ser Asn
    210                 215                 220

Tyr Phe Ala Tyr Glu Thr Gly Asp Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
    290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Val Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
        355                 360                 365

Glu Arg Glu Leu Trp Asp Trp Ala Pro Tyr Glu Asp Val Glu Ile
    370                 375                 380

Gly Pro Asn Gly Val Leu Arg Thr Ser Leu Gly Tyr Lys Phe Pro Leu
385                 390                 395                 400

Tyr Met Ile Gly His Gly Met Leu Asp Ser Asp Leu His Leu Ser Ser
                405                 410                 415
```

```
Lys Ala Gln Val Phe Glu His Pro His Ile Gln Asp Ala Ala Ser Gln
            420                 425                 430

Leu Pro Asp Asp Glu Thr Leu Phe Gly Asp Thr Gly Leu Ser Lys
        435                 440                 445

Asn Pro Ile Glu Phe Val Glu Gly Trp Phe Ser Ser Trp Lys Ser Ser
450                 455                 460

Ile Ala Ser Phe Phe Phe Ile Ile Gly Leu Ile Ile Gly Leu Phe Leu
465                 470                 475                 480

Val Leu Arg Val Gly Ile Tyr Leu Cys Ile Lys Leu Lys His Thr Lys
            485                 490                 495

Lys Arg Gln Ile Tyr Thr Asp Ile Glu Met Asn Arg Leu Gly Lys Met
            500                 505                 510

Gln Gly Asn Thr Cys His Arg Met Ser Phe His Pro Gly Arg Gly Cys
            515                 520                 525

Pro Arg Gly Arg Gly Gly His Gly Ala Arg Pro Ser Ala Pro Ser Phe
530                 535                 540

Arg Pro Gln Asn Leu Arg Leu Leu His Pro Gln Gln Pro Pro Val Gln
545                 550                 555                 560

Tyr Gln Tyr Glu Pro Pro Ser Ala Pro Ser Thr Thr Phe Ser Asn Ser
            565                 570                 575

Pro Ala Pro Asn Phe Leu Pro Pro Arg Pro Asp Phe Val Pro Phe Pro
            580                 585                 590

Pro Pro Met Pro Pro Ser Ala Gln Gly Pro Leu Pro Pro Cys Pro Ile
            595                 600                 605

Arg Pro Pro Phe Pro Asn His Gln Met Arg His Pro Phe Pro Val Pro
            610                 615                 620

Pro Cys Phe Pro Pro Met Pro Pro Met Pro Cys Pro Asn Asn Pro
625                 630                 635                 640

Pro Val Pro Gly Ala Pro Pro Gly Gln Gly Thr Phe Pro Phe Met Met
            645                 650                 655

Pro Pro Pro Ser Met Pro His Pro Pro Pro Pro Val Met Pro Gln
            660                 665                 670

Gln Val Asn Tyr Gln Tyr Pro Pro Gly Tyr Ser His His Asn Phe Pro
            675                 680                 685

Pro Pro Ser Phe Asn Ser Phe Gln Asn Asn Pro Ser Ser Phe Leu Pro
            690                 695                 700

Ser Ala Asn Asn Ser Ser Ser Pro His Phe Arg His Leu Pro Pro Tyr
705                 710                 715                 720

Pro Leu Pro Lys Ala Pro Ser Glu Arg Arg Ser Pro Glu Arg Leu Lys
            725                 730                 735

His Tyr Asp Asp His Arg His Arg Asp His Ser His Gly Arg Gly Glu
            740                 745                 750

Arg His Arg Ser Leu Asp Arg Arg Glu Arg Gly Arg Ser Pro Asp Arg
            755                 760                 765

Arg Arg Gln Asp Ser Arg Tyr Arg Ser Asp Tyr Asp Arg Gly Arg Thr
            770                 775                 780

Pro Ser Arg His Arg Ser Tyr Glu Arg Ser Arg Glu Arg Glu Arg Glu
785                 790                 795                 800

Arg His Arg His Arg Asp Asn Arg Arg Ser Pro Ser Leu Glu Arg Ser
            805                 810                 815

Tyr Lys Lys Glu Tyr Lys Arg Ser Gly Arg Ser Tyr Gly Leu Ser Val
            820                 825                 830
```

-continued

Val Pro Glu Pro Ala Gly Cys Thr Pro Glu Leu Pro Gly Glu Ile Ile
            835                 840                 845

Lys Asn Thr Asp Ser Trp Ala Pro Pro Leu Glu Ile Val Asn His Arg
    850                 855                 860

Ser Pro Ser Arg Glu Lys Lys Arg Ala Arg Trp Glu Glu Lys Asp
865                 870                 875                 880

Arg Trp Ser Asp Asn Gln Ser Ser Gly Lys Asp Lys Asn Tyr Thr Ser
                885                 890                 895

Ile Lys Glu Lys Glu Pro Glu Thr Met Pro Asp Lys Asn Glu Glu
            900                 905                 910

Glu Glu Glu Glu Leu Leu Lys Pro Val Trp Ile Arg Cys Thr His Ser
            915                 920                 925

Glu Asn Tyr Tyr Ser Ser Asp Pro Met Asp Gln Val Gly Asp Ser Thr
    930                 935                 940

Val Val Gly Thr Ser Arg Leu Arg Asp Leu Tyr Asp Lys Phe Glu Glu
945                 950                 955                 960

Glu Leu Gly Ser Arg Gln Glu Lys Ala Lys Ala Ala Arg Pro Pro Trp
                965                 970                 975

Glu Pro Pro Lys Thr Lys Leu Asp Glu Asp Leu Glu Ser Ser Ser Glu
            980                 985                 990

Ser Glu Cys Glu Ser Asp Glu Asp Ser Thr Cys Ser Ser Ser Ser Asp
            995                 1000                1005

Ser Glu Val Phe Asp Val Ile Ala Glu Ile Lys Arg Lys Lys Ala
    1010                1015                1020

His Pro Asp Arg Leu His Asp Glu Leu Trp Tyr Asn Asp Pro Gly
    1025                1030                1035

Gln Met Asn Asp Gly Pro Leu Cys Lys Cys Ser Ala Lys Ala Arg
    1040                1045                1050

Arg Thr Gly Ile Arg His Ser Ile Tyr Pro Gly Glu Glu Ala Ile
    1055                1060                1065

Lys Pro Cys Arg Pro Met Thr Asn Asn Ala Gly Arg Leu Phe His
    1070                1075                1080

Tyr Arg Ile Thr Val Ser Pro Pro Thr Asn Phe Leu Thr Asp Arg
    1085                1090                1095

Pro Thr Val Ile Glu Tyr Asp His Glu Tyr Ile Phe Glu Gly
    1100                1105                1110

Phe Ser Met Phe Ala His Ala Pro Leu Thr Asn Ile Pro Leu Cys
    1115                1120                1125

Lys Val Ile Arg Phe Asn Ile Asp Tyr Thr Ile His Phe Ile Glu
    1130                1135                1140

Glu Met Met Pro Glu Asn Phe Cys Val Lys Gly Leu Glu Leu Phe
    1145                1150                1155

Ser Leu Phe Leu Phe Arg Asp Ile Leu Glu Leu Tyr Asp Trp Asn
    1160                1165                1170

Leu Lys Gly Pro Leu Phe Glu Asp Ser Pro Pro Cys Cys Pro Arg
    1175                1180                1185

Phe His Phe Met Pro Arg Phe Val Arg Phe Leu Pro Asp Gly Gly
    1190                1195                1200

Lys Glu Val Leu Ser Met His Gln Ile Leu Leu Tyr Leu Leu Arg
    1205                1210                1215

Cys Ser Lys Ala Leu Val Pro Glu Glu Glu Ile Ala Asn Met Leu
    1220                1225                1230

Gln Trp Glu Glu Leu Glu Trp Gln Lys Tyr Ala Glu Glu Cys Lys

```
                1235                1240                1245
Gly Met Ile Val Thr Asn Pro Gly Thr Lys Pro Ser Ser Val Arg
    1250                1255                1260

Ile Asp Gln Leu Asp Arg Glu Gln Phe Asn Pro Asp Val Ile Thr
    1265                1270                1275

Phe Pro Ile Ile Val His Phe Gly Ile Arg Pro Ala Gln Leu Ser
    1280                1285                1290

Tyr Ala Gly Asp Pro Gln Tyr Gln Lys Leu Trp Lys Ser Tyr Val
    1295                1300                1305

Lys Leu Arg His Leu Leu Ala Asn Ser Pro Lys Val Lys Gln Thr
    1310                1315                1320

Asp Lys Gln Lys Leu Ala Gln Arg Glu Glu Ala Leu Gln Lys Ile
    1325                1330                1335

Arg Gln Lys Asn Thr Met Arg Arg Glu Val Thr Val Glu Leu Ser
    1340                1345                1350

Ser Gln Gly Phe Trp Lys Thr Gly Ile Arg Ser Asp Val Cys Gln
    1355                1360                1365

His Ala Met Met Leu Pro Val Leu Thr His His Ile Arg Tyr His
    1370                1375                1380

Gln Cys Leu Met His Leu Asp Lys Leu Ile Gly Tyr Thr Phe Gln
    1385                1390                1395

Asp Arg Cys Leu Leu Gln Leu Ala Met Thr His Pro Ser His His
    1400                1405                1410

Leu Asn Phe Gly Met Asn Pro Asp His Ala Arg Asn Ser Leu Ser
    1415                1420                1425

Asn Cys Gly Ile Arg Gln Pro Lys Tyr Gly Asp Arg Lys Val His
    1430                1435                1440

His Met His Met Arg Lys Lys Gly Ile Asn Thr Leu Ile Asn Ile
    1445                1450                1455

Met Ser Arg Leu Gly Gln Asp Asp Pro Thr Pro Ser Arg Ile Asn
    1460                1465                1470

His Asn Glu Arg Leu Glu Phe Leu Gly Asp Ala Val Val Glu Phe
    1475                1480                1485

Leu Thr Ser Val His Leu Tyr Tyr Leu Phe Pro Ser Leu Glu Glu
    1490                1495                1500

Gly Gly Leu Ala Thr Tyr Arg Thr Ala Ile Val Gln Asn Gln His
    1505                1510                1515

Leu Ala Met Leu Ala Lys Lys Leu Glu Leu Asp Arg Phe Met Leu
    1520                1525                1530

Tyr Ala His Gly Pro Asp Leu Cys Arg Glu Ser Asp Leu Arg His
    1535                1540                1545

Ala Met Ala Asn Cys Phe Glu Ala Leu Ile Gly Ala Val Tyr Leu
    1550                1555                1560

Glu Gly Ser Leu Glu Glu Ala Lys Gln Leu Phe Gly Arg Leu Leu
    1565                1570                1575

Phe Asn Asp Pro Asp Leu Arg Glu Val Trp Leu Asn Tyr Pro Leu
    1580                1585                1590

His Pro Leu Gln Leu Gln Glu Pro Asn Thr Asp Arg Gln Leu Ile
    1595                1600                1605

Glu Thr Ser Pro Val Leu Gln Lys Leu Thr Glu Phe Glu Glu Ala
    1610                1615                1620

Ile Gly Val Ile Phe Thr His Val Arg Leu Leu Ala Arg Ala Phe
    1625                1630                1635
```

-continued

```
Thr Leu Arg Thr Val Gly Phe Asn His Leu Thr Leu Gly His Asn
    1640                1645                1650

Gln Arg Met Glu Phe Leu Gly Asp Ser Ile Met Gln Leu Val Ala
    1655                1660                1665

Thr Glu Tyr Leu Phe Ile His Phe Pro Asp His His Glu Gly His
    1670                1675                1680

Leu Thr Leu Leu Arg Ser Ser Leu Val Asn Asn Arg Thr Gln Ala
    1685                1690                1695

Lys Val Ala Glu Glu Leu Gly Met Gln Glu Tyr Ala Ile Thr Asn
    1700                1705                1710

Asp Lys Thr Lys Arg Pro Val Ala Leu Arg Thr Lys Thr Leu Ala
    1715                1720                1725

Asp Leu Leu Glu Ser Phe Ile Ala Ala Leu Tyr Ile Asp Lys Asp
    1730                1735                1740

Leu Glu Tyr Val His Thr Phe Met Asn Val Cys Phe Phe Pro Arg
    1745                1750                1755

Leu Lys Glu Phe Ile Leu Asn Gln Asp Trp Asn Asp Pro Lys Ser
    1760                1765                1770

Gln Leu Gln Gln Cys Cys Leu Thr Leu Arg Thr Glu Gly Lys Glu
    1775                1780                1785

Pro Asp Ile Pro Leu Tyr Lys Thr Leu Gln Thr Val Gly Pro Ser
    1790                1795                1800

His Ala Arg Thr Tyr Thr Val Ala Val Tyr Phe Lys Gly Glu Arg
    1805                1810                1815

Ile Gly Cys Gly Lys Gly Pro Ser Ile Gln Gln Ala Glu Met Gly
    1820                1825                1830

Ala Ala Met Asp Ala Leu Glu Lys Tyr Asn Phe Pro Gln Met Ala
    1835                1840                1845

His Gln Lys Arg Phe Ile Glu Arg Lys Tyr Arg Gln Glu Leu Lys
    1850                1855                1860

Glu Met Arg Trp Glu Arg Glu His Gln Glu Arg Glu Pro Asp Glu
    1865                1870                1875

Thr Glu Asp Ile Lys Lys
    1880
```

CHIMERIC VSV-G PROTEINS AS NUCLEIC ACID TRANSFER VEHICLES

CROSS-REFERENCE TO RELATED APPLICATIONS

This application claims the benefit of U.S. Provisional Patent No. 61/984,290, filed Apr. 25, 2014, which is incorporated by reference herein in its entirety.

FIELD OF THE DISCLOSURE

What is disclosed is a chimeric or fusion protein including a membrane transport domain and a nucleic acid binding domain allowing targeted delivery of nucleic acids in humans and animals for the treatment of medical conditions.

BACKGROUND OF THE DISCLOSURE

The vesicular stomatitis virus G glycoprotein (hereinafter referred to as "VSV-G") is widely used to pseudotype viral vectors due to its wide tropism and stability. These viral vectors facilitate gene transduction in human and animals. The VSV-G proteins, when not associated with any viral vectors, are also alone capable of forming complexes with naked plasmid DNA in cell free conditions which can be transfected to cells thereafter.

The fusogenic G glycoprotein of the vesicular stomatitis virus has proved to be a useful tool for viral-mediated gene delivery by acting as an envelope protein. Due to its wide tropism, VSV-G has been used as an efficient surrogate envelope protein to produce more stable and high titer pseudotyped murine leukemia virus (MLV)-based retrovirus and lentivirus-based vectors, all of which have been effectively used for gene therapy. The reason behind this pantropism of VSV remained elusive for a long period. Recently, it has been found that the VSV enters the cell through a highly ubiquitous low-density lipoprotein (LDL) receptor having wide distribution.

However, there are some limitations associated with the use of VSV-G. It is cytotoxic to producer cells, though the use of tetracycline-regulated promoters has helped to overcome this problem. In addition, serum inactivation of VSV-G pseudotyped viruses poses a problem and impedes their function to some extent in vivo. To overcome the latter problem, VSV-G mutants have been generated which are more thermostable as well as serum-resistant. VSV-G mutants harboring T230N+T368A or K66T+S162T+T230N+T368A mutations exhibited more resistance to serum inactivation and higher thermostability.

Apart from acting as a fusogenic envelope protein for many viral vectors, previous studies showed that purified soluble VSV-G itself can be inserted into lipid bilayers of liposomes and lipid vesicles in cell free system in vitro. Additionally, it has been shown that VSV-G can form a complex with naked plasmid DNA in the absence of any transfection reagent and can thereby enhance the transfection of naked plasmid DNA into cells. Sucrose gradient sedimentation analysis demonstrated that VSV-G associates with plasmid DNA and MLV gag-pol particles to form ternary complexes that co-sediment with high DNA transfecting activity. This transfection could be abolished by adding antibody for VSV-G.

In eukaryotic cells, heritable genetic material is packaged into structures known as chromatin consisting of DNA and protein. The basic repeating unit of chromatin is the nucleosome core, which consists of 147 base pairs of DNA wrapped in 1.7 left-handed superhelical turns around the surface of an octameric protein core formed by two molecules each of histones H2A, H2B, H3, and H4. Histones are highly basic proteins that bind very avidly and non-specifically to nucleic acids. Histones were among the first proteins studied due to their relative ease of isolation and all four histone proteins (H2A, H2B, H3, and H4) can be expressed in bacteria. This has allowed purifying and reconstituting of the histone proteins in cell free systems using well defined protocols. Though the native histone proteins undergo an extensive array of posttranslational modifications, recombinant histones do not undergo posttranslational modifications and can be obtained in a highly pure form due to their high expression levels.

Single Strand DNA-Binding Proteins (hereinafter referred to as "SSBP") are ubiquitously expressed and involved in a variety of DNA metabolic processes including replication, recombination, damage, and repair. SSBP-1 is a housekeeping gene involved in mitochondrial biogenesis. It is also a subunit of a single-stranded DNA (ssDNA)-binding complex involved in the maintenance of genome stability.

Ribonuclease III (hereinafter referred to as "RNase III") is an enzyme that is expressed in most of the cells and is involved in the processing of pre-rRNA. It has a catalytic domain and an RNA binding domain that is located in the C-terminal end of the enzyme. Inhibition of human RNase III resulted in cell death suggesting a very important role of this enzyme.

Gene therapy and exon skipping have served as a means of gene transduction or gene manipulation respectively in humans during the past two decades. Gene therapy and exon skipping were initially developed as therapeutic strategies focused to address detrimental monogenetic diseases for which there were no available options for treatment, e.g. primary immunodeficiency. These approaches later found widespread application in curing neurodegenerative diseases, cancer, metabolic disorders, and more.

Gene therapy involves delivery of genes of interest cloned in viral vectors which are capable of producing viruses when transduced in human cells. Despite the continuous improvement of retroviral and lentiviral gene transfer systems for gene delivery during the last many years, there remain severe limitations preventing the development of efficient and safe clinical applications for these systems. These limitations include: their inability to target infection to cells of interest, inefficient transduction, propensity of viral vectors to get incorporated in human genome and create mutations, elicited high immune responses, inability to be administered intravenously or subcutaneously, and intramuscular administration that only leads to local delivery of the gene. Owing to these limitations, no gene therapy based medication has been approved by FDA for use in humans, though there have been many clinical trials during the past two decades and also many ongoing clinical trials.

Exon skipping is a therapeutic strategy where antisense oligonucleotides (AO) are delivered in humans to modulate splicing of genes resulting in mRNA that either produces functional proteins or blocks their production. AOs are short nucleic acid sequences designed to selectively bind to specific mRNA or pre-mRNA sequences. Despite the very convincing underlying principle behind this strategy, only one AO has been approved by the FDA (Vitravene™, an intraocular injection to inhibit cytomegalovirus retinitis in immunocompromised patients; Isis Pharmaceuticals, Carlsbad, Calif.), and this drug is no longer marketed. There are certain limitations associated with the use of AOs including difficulty in achieving pharmacologically significant concentrations in cells due to biological barriers like endothelial and basement membrane, cell membrane, and sequestration by phagolysosomes.

Further discussion on the subjects of gene transfer and delivery may be found in U.S. Pat. No. 7,531,647 ("Lentiviral Vectors for Site-Specific Gene Insertion"); U.S. Pat. No. 8,158,827 ("Transfection Reagents"); and U.S. Pat. No. 8,652,460 ("Gene Delivery System and Method of Use") and U.S. patent application Ser. No. 14/635,012 ("Chimeric Dystrophin-VSV-G Protein to Treat Dystrophinopathies". The disclosures of each of U.S. Pat. Nos. 7,531,647, 8,158,827 and 8,652,460 and U.S. application Ser. No. 14/635,012 are incorporated by reference herein in their entireties.

The details of one or more embodiments of the invention are set forth in the accompanying drawings and the description below. Other features, objects and advantages of the invention will be apparent from the description and drawings, and from the claims.

BRIEF SUMMARY OF THE INVENTION

Disclosed herein is a chimeric protein incorporating a transport domain and a nucleic acid binding domain and methods of utilizing those chimeric proteins for targeted delivery of therapeutic nucleic acids.

In some embodiments, the present disclosure is directed to a chimeric protein comprising VSV-G and a nucleic acid binding protein. In some embodiments, the nucleic acid binding protein is a histone. In some embodiments, the histone is selected from the group consisting of: H2A, H2B, H3, and H4. In some embodiments, the histone is tagged with VSV-G at the C-terminus. In some embodiments, histone is tagged with VSV-G at the N-terminus.

In some embodiments, the chimeric protein comprises SEQ. ID NO.: 1, SEQ. ID NO.: 2, SEQ. ID NO.: 3, SEQ. ID NO.: 4, SEQ. ID NO.: 5, SEQ. ID NO.: 6, SEQ. ID NO.: 7, or SEQ. ID NO.: 8, and pharmacologically acceptable equivalents thereof. In some embodiments, the chimeric protein comprises SEQ. ID NO.: 15, SEQ. ID NO.: 16, SEQ. ID NO.: 17, SEQ. ID NO.: 18, SEQ. ID NO.: 19, SEQ. ID NO.: 20, SEQ. ID NO.: 21, or SEQ. ID NO.: 22, and pharmacologically acceptable equivalents thereof. In some embodiments, the chimeric protein includes a sequence having at least 90%, at least 95%, at least 96%, at least 97%, at least 98%, or at least 99% sequence identity with SEQ. ID NO.: 1, SEQ. ID NO.: 2, SEQ. ID NO.: 3, SEQ. ID NO.: 4, SEQ. ID NO.: 5, SEQ. ID NO.: 6, SEQ. ID NO.: 7, or SEQ. ID NO.: 8. In some embodiments, the chimeric protein includes a sequence having at least 90%, at least 95%, at least 96%, at least 97%, at least 98%, or at least 99% sequence identity with SEQ. ID NO.: 15, SEQ. ID NO.: 16, SEQ. ID NO.: 17, SEQ. ID NO.: 18, SEQ. ID NO.: 19, SEQ. ID NO.: 20, SEQ. ID NO.: 21, or SEQ. ID NO.: 22.

In some embodiments, the nucleic acid binding protein is SSBP-1. In some embodiments, SSBP-1 is tagged with VSV-G at the C-terminus. In some embodiments, SSBP-1 is tagged with VSV-G at the N-terminus. In some embodiments, the chimeric protein comprises SEQ. ID NO.: 9 or SEQ. ID NO.: 10, and pharmacologically acceptable equivalents thereof. In some embodiments, the chimeric protein comprises SEQ. ID NO.: 23 or SEQ. ID NO.: 24, and pharmacologically acceptable equivalents thereof. In some embodiments, the chimeric protein includes a sequence having at least 90%, at least 95%, at least 96%, at least 97%, at least 98%, or at least 99% sequence identity with SEQ. ID NO.: 9 or SEQ. ID NO.: 10. In some embodiments, the chimeric protein includes a sequence having at least 90%, at least 95%, at least 96%, at least 97%, at least 98%, or at least 99% sequence identity with SEQ. ID NO.: 23 or SEQ. ID NO.: 24.

In some embodiments, the nucleic acid binding protein is RNase III. In some embodiments, RNase III is tagged with VSV-G at the C-terminus. In some embodiments, RNase III is tagged with VSV-G at the N-terminus. In some embodiments, the chimeric protein comprises SEQ. ID NO.: 11, SEQ. ID NO.: 12, or SEQ. ID NO.: 13, and pharmacologically acceptable equivalents thereof. In some embodiments, wherein the chimeric protein comprises SEQ. ID NO.: 14, SEQ. ID NO.: 25, or SEQ. ID NO.: 26, and pharmacologically acceptable equivalents thereof. In some embodiments, wherein the chimeric protein includes a sequence having at least 90%, at least 95%, at least 96%, at least 97%, at least 98%, or at least 99% sequence identity with SEQ. ID NO.: 11, SEQ. ID NO.: 12, or SEQ. ID NO.: 13. In some embodiments, wherein the chimeric protein includes a sequence having at least 90%, at least 95%, at least 96%, at least 97%, at least 98%, or at least 99% sequence identity with SEQ. ID NO.: 14, SEQ. ID NO.: 25, or SEQ. ID NO.: 26.

In some embodiments, the present disclosure is directed to a method of treating a medical condition in a subject comprising the steps of providing a therapeutic compound comprising a chimeric protein including VSV-G, a nucleic acid binding protein, and at least one nucleic acid, and administering to said subject a pharmaceutically active amount of said therapeutic compound. In some embodiments, the present disclosure is directed to a therapeutic compound comprising a chimeric protein as described herein.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention will be apparent from the following detailed description taken in conjunction with the accompanying drawings.

FIG. 5 portrays a method of treating a medical condition using a chimeric protein such as that isolated in FIG. 1.

DETAILED DESCRIPTION

Figure 1:
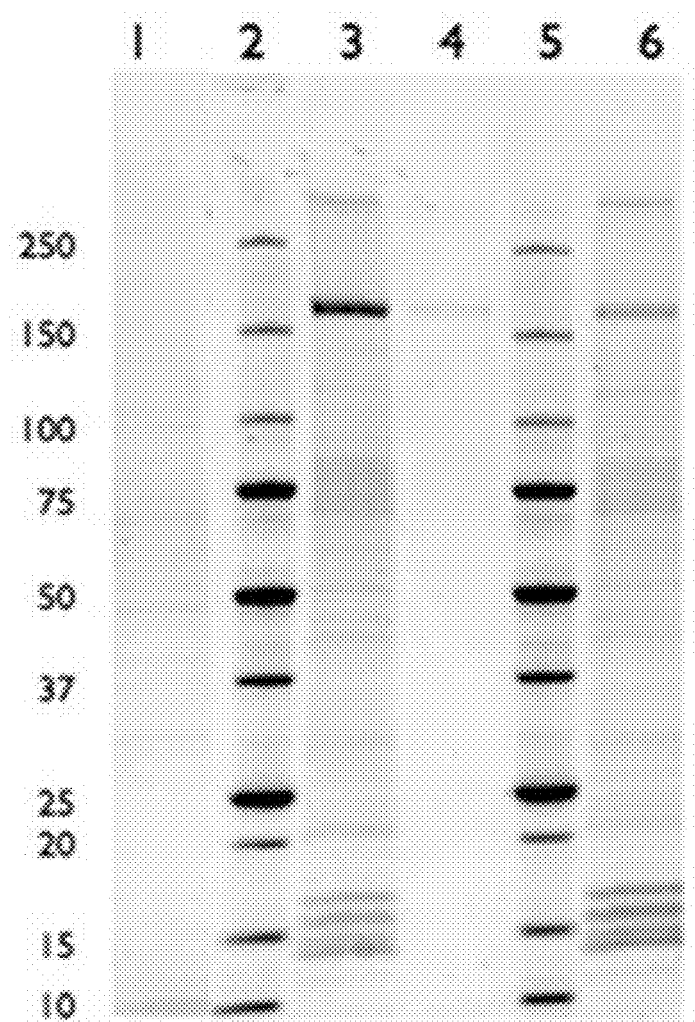
FIG. 1 portrays chimeric VSV-G H2A protein fractions purified by SDS-PAGE analysis.

In some embodiments, the present disclosure is directed to a number of chimeric VSV-G (or VSV-G variants) proteins comprising VSV-G and at least one nucleic acid binding protein. In some embodiments, these proteins are used as transfer vehicles to enhance delivery of nucleic acids like plasmid DNA, single and double stranded DNA and RNA, and antisense oligonucleotides into human and animal cells.

VSV-G cloned in expression plasmids, when transfected in cells, form sedimetable vesicles in the absence of any viral components. The chimeric proteins described here efficiently complex with nucleic acids in cell free systems and can be used as an effective means for delivering AOs and genes of interest in human and animal cells. This approach mitigates a number of risks and issues that are associated with gene therapy and exon skipping, i.e. there is no risk of toxicity related to viral production or risk of viral genome incorporation and possible mutations arising as a result. Since the VSV-G proteins enter into cells via the LDL receptors which are almost ubiquitously expressed, the transduction efficiency of the chimeric VSV-G-nucleic acid transfer vehicle is higher than that achieved by exon-skipping. The chimeric VSV-G-nucleic acid transfer vehicle consistent with some embodiments of the present disclosure can also replace the current mechanism of gene therapy. As this proposed chimeric VSV-G-nucleic acid transfer vehicle does not rely on virus production, it has fewer side effects and can be administered subcutaneously. This system can be used for gene replacement and can have wide application to cure many disorders arising from genetic mutations.

In some embodiments, wild-type VSV-G is used in the chimeric protein. In some embodiments, VSV-G variants are used in the chimeric protein. In some embodiments, the VSV-G variants include the thermostable and serum resistant mutants of VSV-G, e.g. S162T, T230N, T368A, or combined mutants T230N+T368A or K66T+S162T+T230N+T368A. In some embodiments, variant VSV-G has at least 90%, at least 95%, at least 96%, at least 97%, at least 98%, or at least 99% sequence identity with wild-type VSV-G. As used in the following embodiments, the term "VSV-G" refers to both wild-type VSV-G and VSV-G variants.

In some embodiments, the chimeric protein of the present disclosure has at least 90%, at least 95%, at least 96%, at least 97%, at least 98%, or at least 99% sequence identity with the combined sequence of VSV-G+nucleic acid binding protein, with the nucleic acid binding protein tagged with VSV-G at the C-terminus. In some embodiments, chimeric protein has at least 90%, at least 95%, at least 96%, at least 97%, at least 98%, or at least 99% sequence identity with the combined sequence of VSV-G+nucleic acid binding protein, with the nucleic acid binding protein tagged with VSV-G at the N-terminus. In some embodiments, the chimeric protein comprises a nucleotide sequence that has at least 90%, at least 95%, at least 96%, at least 97%, at least 98%, or at least 99% sequence identity with at least one of SEQ. ID NO.: 1, SEQ. ID NO.: 3, SEQ. ID NO.: 5, SEQ. ID NO.: 7, SEQ. ID NO.: 9, SEQ. ID NO.: 11, SEQ. ID NO.: 13, SEQ. ID NO.: 15, SEQ. ID NO.: 17, SEQ. ID NO.: 19, SEQ. ID NO.: 21, SEQ. ID NO.: 23, or SEQ. ID NO.: 25. In some embodiments, the chimeric protein comprises an amino acid sequence that has at least 90%, at least 95%, at least 96%, at least 97%, at least 98%, or at least 99% sequence identity with at least one of SEQ. ID NO.: 2, SEQ. ID NO.: 4, SEQ. ID NO.: 6, SEQ. ID NO.: 8, SEQ. ID NO.: 10, SEQ. ID NO.: 12, SEQ. ID NO.: 14, SEQ. ID NO.: 16, SEQ. ID NO.: 18, SEQ. ID NO.: 20, SEQ. ID NO.: 22, SEQ. ID NO.: 24, or SEQ. ID NO.: 26. In some embodiments, any suitable mutations, substitutions, additions, and deletions may be made to the chimeric protein so long as the pharmacological activity of the resulting variant chimeric protein is retained.

In some embodiments, the nucleic acid binding protein is selected from the group consisting of H2A histone, H2B histone, H3 histone, H4 histone, SSBP-1, RNase III, and combinations thereof.

SEQ. ID NO: 1 is a nucleotide sequence of an H2A histone-VSV-G chimeric protein, with VSV-G at the C-terminus, consistent with some embodiments of the present disclosure.

SEQ. ID NO: 2 is an amino acid sequence of an H2A histone-VSV-G chimeric protein, with VSV-G at the C-terminus, consistent with some embodiments of the present disclosure.

SEQ. ID NO: 3 is a nucleotide sequence of an H2B histone-VSV-G chimeric protein, with VSV-G at the C-terminus, consistent with some embodiments of the present disclosure.

SEQ. ID NO: 4 is an amino acid sequence of an H2B histone-VSV-G chimeric protein, with VSV-G at the C-terminus, consistent with some embodiments of the present disclosure.

SEQ. ID NO: 5 is a nucleotide sequence of an H3 histone-VSV-G chimeric protein, with VSV-G at the C-terminus, consistent with some embodiments of the present disclosure.

SEQ. ID NO: 6 is an amino acid sequence of an H3 histone-VSV-G chimeric protein, with VSV-G at the C-terminus, consistent with some embodiments of the present disclosure.

SEQ. ID NO: 7 is a nucleotide sequence of an H4 histone-VSV-G chimeric protein, with VSV-G at the C-terminus, consistent with some embodiments of the present disclosure.

SEQ. ID NO: 8 is an amino acid sequence of an H4 histone-VSV-G chimeric protein, with VSV-G at the C-terminus, consistent with some embodiments of the present disclosure.

SEQ. ID NO: 9 is a nucleotide sequence of an SSBP-1-VSV-G chimeric protein, with VSV-G at the C-terminus, consistent with some embodiments of the present disclosure.

SEQ. ID NO: 10 is an amino acid sequence of an SSBP-1-VSV-G chimeric protein, with VSV-G at the C-terminus, consistent with some embodiments of the present disclosure.

SEQ. ID NO: 11 is a nucleotide sequence of an RNase III-VSV-G chimeric protein, with VSV-G at the C-terminus, consistent with some embodiments of the present disclosure.

SEQ. ID NO: 12 is an amino acid sequence of an RNase III-VSV-G chimeric protein, with VSV-G at the C-terminus, consistent with some embodiments of the present disclosure.

SEQ. ID NO: 13 is a nucleotide sequence of a partial RNase III-VSV-G chimeric protein, with VSV-G at the N-terminus, consistent with some embodiments of the present disclosure.

SEQ. ID NO: 14 is an amino acid sequence of a partial RNase III-VSV-G chimeric protein, with VSV-G at the N-terminus, consistent with some embodiments of the present disclosure.

SEQ. ID NO: 15 is a nucleotide sequence of an H2A histone-VSV-G chimeric protein, with VSV-G at the N-terminus, consistent with some embodiments of the present disclosure.

SEQ. ID NO: 16 is an amino acid sequence of an H2A histone-VSV-G chimeric protein, with VSV-G at the N-terminus, consistent with some embodiments of the present disclosure.

SEQ. ID NO: 17 is a nucleotide sequence of an H2B histone-VSV-G chimeric protein, with VSV-G at the N-terminus, consistent with some embodiments of the present disclosure.

SEQ. ID NO: 18 is an amino acid sequence of an H2B histone-VSV-G chimeric protein, with VSV-G at the N-terminus, consistent with some embodiments of the present disclosure.

SEQ. ID NO: 19 is a nucleotide sequence of an H3 histone-VSV-G chimeric protein, with VSV-G at the N-terminus, consistent with some embodiments of the present disclosure.

SEQ. ID NO: 20 is an amino acid sequence of an H3 histone-VSV-G chimeric protein, with VSV-G at the N-terminus, consistent with some embodiments of the present disclosure.

SEQ. ID NO: 21 is a nucleotide sequence of an H4 histone-VSV-G chimeric protein, with VSV-G at the N-terminus, consistent with some embodiments of the present disclosure.

SEQ. ID NO: 22 is an amino acid sequence of an H4 histone-VSV-G chimeric protein, with VSV-G at the N-terminus, consistent with some embodiments of the present disclosure.

SEQ. ID NO: 23 is a nucleotide sequence of an SSBP-1-VSV-G chimeric protein, with VSV-G at the N-terminus, consistent with some embodiments of the present disclosure.

SEQ. ID NO: 24 is an amino acid sequence of an SSBP-1-VSV-G chimeric protein, with VSV-G at the N-terminus, consistent with some embodiments of the present disclosure.

SEQ. ID NO: 25 is a nucleotide sequence of an RNase III-VSV-G chimeric protein, with VSV-G at the N-terminus, consistent with some embodiments of the present disclosure.

SEQ. ID NO: 26 is an amino acid sequence of an RNase III-VSV-G chimeric protein, with VSV-G at the N-terminus, consistent with some embodiments of the present disclosure.

In some embodiments, the present disclosure is directed to a therapeutic compound comprising a chimeric protein consistent with those described in the above-identified embodiments. In some embodiments, as shown in FIG. 5, the present disclosure is directed to a method of treating a medical condition within a subject. In some embodiments, the method of treating a subject comprises the steps of providing 500 a therapeutic compound comprising a chimeric protein including VSV-G, a nucleic acid binding protein, and at least one nucleic acid, and administering 510 to the subject a pharmaceutically active amount of the therapeutic compound. In some embodiments, at least one nucleic acid is a therapeutic gene.

EXAMPLE

The following example utilizes a VSV-G-H2A chimeric protein constructed from a human histone H2A protein tagged with VSV-G at the N-terminus. The VSV-G-H2A chimeric gene was synthesized using the propriety technology from Integrated DNA Technologies, Skokie, Ill. The VSV-G-H2A gene was cloned in the mammalian expression vector pTT5 at EcoRI and NotI restriction enzyme sites. The plasmid was prepared and sequenced for confirmation.

HEK293T cells were passed to ~70% confluency a day prior to transfection (3×T75 flasks, ~7.5×10$^6$ cells/flask). The following day, the cells in T75 flasks were transfected using Lipofectamine® 2000 (Life Technologies Corp., Carlsbad, Calif.) (per T75 flask: 3:1 ratio; 20 ug DNA; and 60 µL Lipofectamine® 2000). Flasks were incubated at 37° C. and 5% CO$_2$ overnight. 24 hours after transfection, the conditioned media was removed and replaced with fresh media (14 mL/flask). Cells were further incubated overnight. Conditioned media was harvested and replaced with fresh media (14 mL/flask) and again incubated overnight. Harvested media was then filtered using 0.45 µm filter and stored at −80° C. The following day, conditioned media was harvested again and filtered using 0.45 µm filter. Conditioned media was pooled with media from the previous day (~84 mL).

Conditioned media was centrifuged using the Optima® Ultra Centrifuge (with swinging bucket rotor SW32Ti) (Beckman Coulter, Inc., Brea, Calif.) at 25,000 rpm for 2 h at 4° C. (3 centrifuge tubes, ~28 mL/tube). Supernatant was removed and pellets were resuspended in 5 mL PBS per tube. 5 mL of 20% sucrose/PBS cushion plus 5 mL resuspended pellet was added to a new centrifuge tube. PBS was overlaid to fill the centrifuge tube. Samples were centrifuged at 25,000 rpm for 6 hours at 4° C. Supernatant was removed and each pellet was resuspended in 100 µL PBS (300 µL total volume). An additional 100 µL of PBS was added to each centrifuge tube to resuspend any remaining VSV-G-H2A protein (300 µL total volume). Protein concentration was measured by A660 Assay.

The chimeric VSV-G H2A protein fractions thus purified were run on polyacrylamide gels before transfer to nitrocellulose membranes. Proteins were run in 4-15% BioRad TGX™ gel (BioRad Laboratories Inc., Hercules, Calif.) with BioRad Precision Plus Protein™ markers, at 300 V for 21 minutes and then stained with SYPRO®-Orange stain (Molecular Probes, Inc., Eugene, Oreg.), the results of which can be seen at FIG. 1. The contents for each lane found in FIG. 1 are as follows: Lane 1: Negative Control—untransfected cells only; Lane 2: molecular weight marker; Lane 3: M20336-01 (20 µL load); Lane 4: M20336-01 (2 µL load); Lane 5: molecular weight marker; and Lane 6: M20336-02 (20 µL load). The HEK293 untransfected lane did not stain for any protein while rest of the lanes containing the fractions of purified VSV-G-H2A chimeric protein stained for proteins confirming the presence of purified proteins in the fractions.

Figure 2:
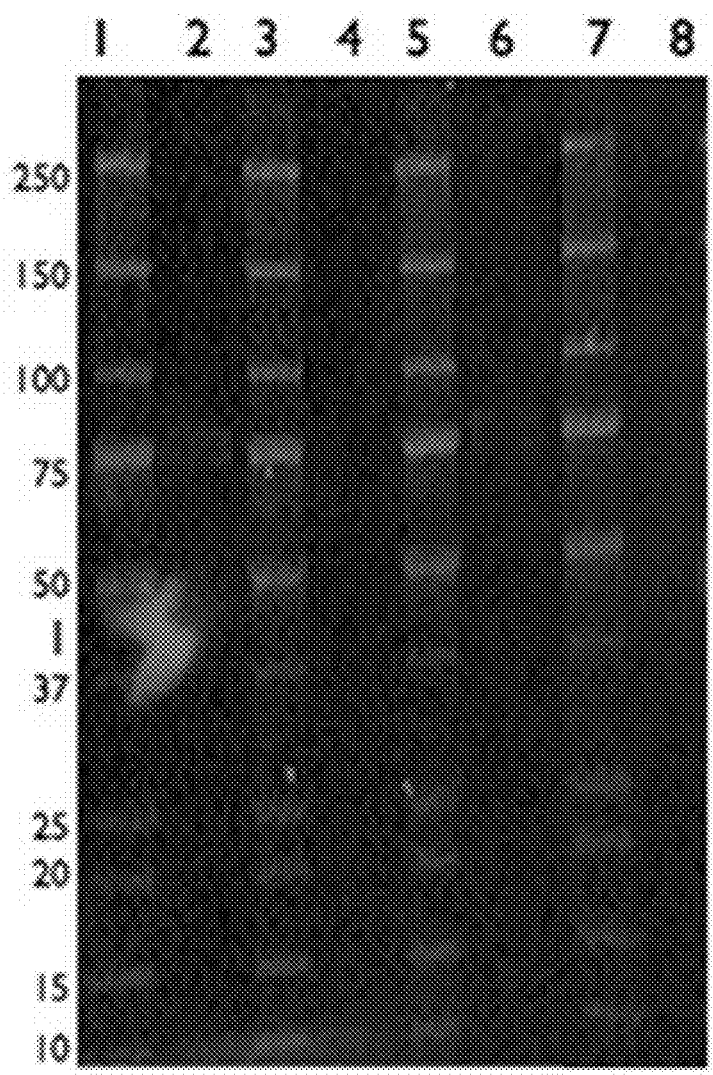
FIG. 2 portrays western blot analysis of the proteins in the purified fractions from SDS-PAGE analysis as seen in FIG. 1.

After confirming the presence of the proteins in the purified fractions, proteins were run using the same conditions as described above and transferred to nitrocellulose membrane. The chimeric VSV-G-H2A protein was detected by probing with anti-VSV-G-primary antibody and anti-rabbit HRP secondary antibody. Proteins were transferred to nitrocellulose membrane using Bio-Rad Trans-Blot® Turbo™. Signal was detected using the SNAP id® system (Merck KGAA, Darmstadt, Del.) and SuperSignal® West Pico chemiluminescent substrate (Pierce Biotechnology, Inc., Rockford, Ill.), the results of which can be seen in the western blot shown in FIG. 2. The contents for each lane found in FIG. 2 are as follows: Lane 1: molecular weight marker; Lane 2: M20336-01 (20 µL load); Lane 3: molecular weight marker; Lane 4: M20336-01 (2 µL load); Lane 5: molecular weight marker; Lane 6: M20336-02 (20 µL load); Lane 7: molecular weight marker; Lane 8: Negative Control—untransfected cells only. A band was detected specific to the size of VSV-G H2A chimeric protein at 75 kD in lanes 2 and 6 containing 20 µL load of protein. No bands were detected in lanes 4 and 8 with 2 µL load of purified protein fraction and non-transfected HEK293 protein fraction. Therefore, the presence of VSV-G-H2A chimeric protein in the purified fraction was confirmed.

Figure 3:
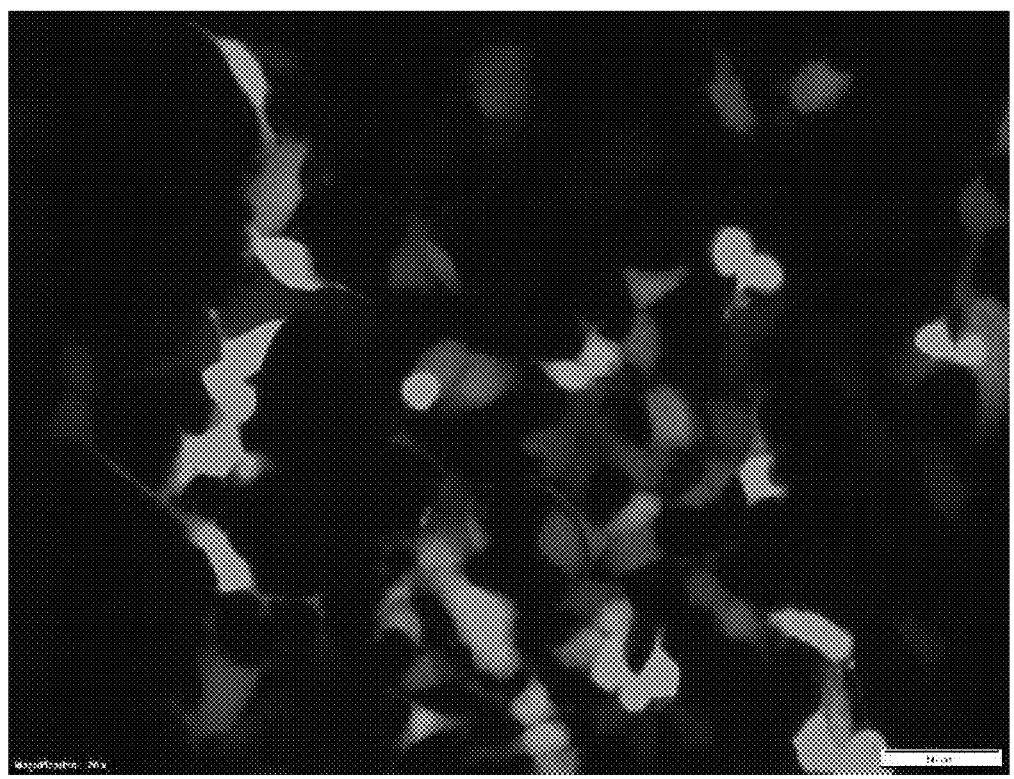
FIG. 3 portrays expression of GFP:HEK 293 cells transfected with eGFPN1 plasmid.

In order to evaluate the capacity of the purified VSV-G-H2A chimeric protein to act as nucleic acid transfer vehicle, HEK293 cells and NIH 3T3 cells were transfected with green fluorescent protein (GFP) expressing plasmid eGFPN1 utilizing the VSV-G-H2A chimeric protein. Firstly, the eGFPN1 plasmid was transfected in HEK293 cells using ViaFect™ transfection reagent (Promega Corp., Madison, Wis.) to confirm that GFP was expressed properly. Successful GFP expression is shown in FIG. 3.

Figure 4A:
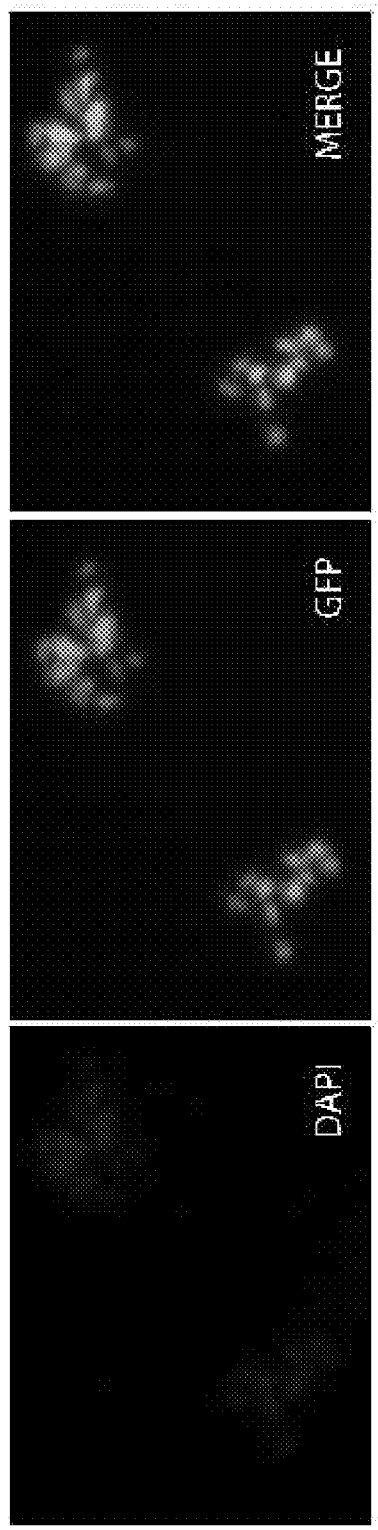
FIG. 4A portrays GFP-including plasmid eGFPN1 transfected in HEK293 cells using purified VSV-G-H2A protein.
Figure 4B:
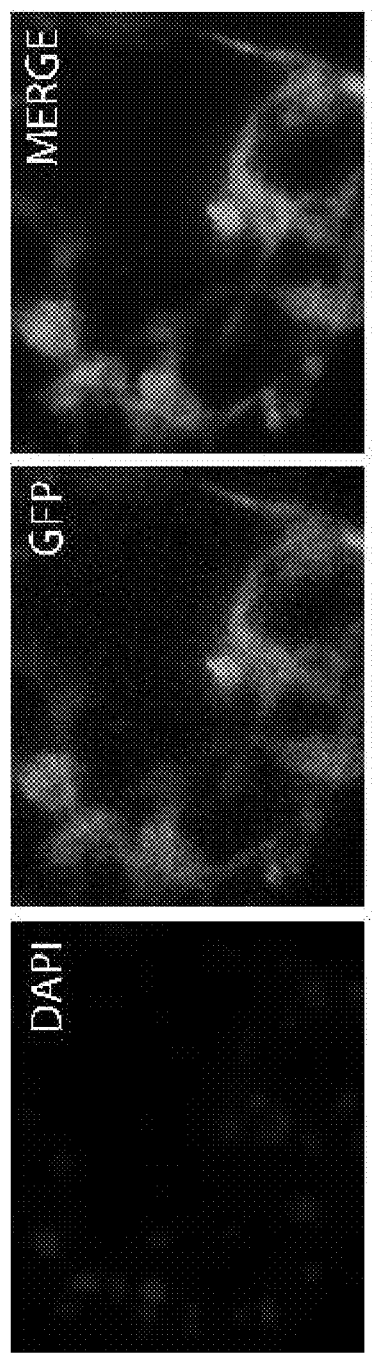
FIG. 4B portrays GFP-including plasmid eGFPN1 transfected in NIH 3T3 cells using purified VSV-G-H2A protein.

To determine whether similar expression of GFP could be seen when VSV-G-H2A chimeric protein was used as a transfer vehicle, 2 µg of eGFPN1 plasmid was mixed with 3 µg of VSV-G H2A purified chimeric protein and overlaid in each of HEK293 and NIH 3T3 cells seeded on coverslips in 6-well plates. Cells were incubated for 48 hours before analysis. To detect whether GFP has expressed, the existing medium in the cells was aspirated, washed in Dulbecco's phosphate buffered saline (DPBS), and then fixed in 4% paraformaldehyde solution. Cells were washed again with DPBS a couple of times, stained with 4',6-diamidino-2-phenylindole (DAPI), and then mounted in appropriate mounting medium and viewed under a fluorescence microscope. The results of this procedure can be seen in FIGS. 4A and 4B, wherein DAPI staining depicts the nucleus and the green fluorescence depicts the GFP. Interestingly, the HEK293 and NIH 3T3 cells in which VSV-G-H2A purified chimeric protein was used as a transfer vehicle to transfect eGFPN1 plasmid expressed GFP. Therefore, it was concluded that VSV-G-H2A chimeric protein, as well as the other chimeric proteins disclosed in the present disclosure and functional equivalents thereof, are candidates for use as nucleic acid transfer vehicles as proposed by the present disclosure.

One or more embodiments of the present invention have been described. Nevertheless, it will be understood that various modifications may be made without departing from the spirit and scope of the invention. Accordingly, other embodiments are within the scope of the following claims.

What is claimed is:

1. A chimeric protein comprising a vesicular stomatitis virus G glycoprotein (VSV-G) and a nucleic acid binding protein selected from the group consisting of histones, Single Strand DNA-Binding Protein-1 (SSBP-1), and RNaseIII.

2. The chimeric protein according to claim 1, wherein the nucleic acid binding protein is a histone.

3. The chimeric protein according to claim 2, wherein the histone is selected from the group consisting of: H2A, H2B, H3, and H4.

4. The chimeric protein according to claim 2, wherein the histone is tagged with VSV-G at the C-terminus.

5. The chimeric protein according to claim 2, wherein the histone is tagged with VSV-G at the N-terminus.

6. The chimeric protein according to claim 4, wherein the chimeric protein is one selected from the group consisting of SEQ ID NO: 2, SEQ ID NO: 4, SEQ ID NO: 6, and SEQ ID NO: 8.

7. The chimeric protein according to claim 5, wherein the chimeric protein is one selected from the group consisting of SEQ ID NO: 16, SEQ ID NO: 18, SEQ ID NO: 20, and SEQ ID NO: 22.

8. The chimeric protein according to claim 4, wherein the chimeric protein includes a sequence having at least 90% sequence identity with SEQ ID NO: 2, SEQ ID NO: 4, SEQ ID NO: 6 or SEQ ID NO: 8.

9. The chimeric protein according to claim 5, wherein the chimeric protein includes a sequence having at least 90% sequence identity with SEQ ID NO: 16, SEQ ID NO: 18, SEQ ID NO: 20 or SEQ ID NO: 22.

10. A therapeutic compound comprising the chimeric protein according to claim 1.

11. The chimeric protein according to claim 6, wherein the chimeric protein is encoded by a nucleic acid sequence selected from the group consisting of: SEQ ID NO: 1, 3, 5 and 7.

12. The chimeric protein according to claim 7, wherein the chimeric protein is encoded by a nucleic acid sequence selected from the group consisting of: SEQ ID NO: 16, 18, 20 and 22.

13. The chimeric protein according to claim 8, wherein the chimeric protein is encoded by a nucleic acid sequence selected from the group consisting of: SEQ ID NO: 1, 3, 5 and 7.

14. The chimeric protein according to claim 9, wherein the chimeric protein is encoded by a nucleic acid sequence selected from the group consisting of: SEQ ID NO: 16, 18, 20 and 22.

15. A chimeric protein consisting of a vesicular stomatitis virus G glycoprotein (VSV-G) and a nucleic acid binding protein selected from the group consisting of histones, SSBP-1 and RNase III.

16. A method of treating a medical condition in a subject comprising the steps of:
   providing a therapeutic compound comprising a chimeric protein comprising a vesicular stomatitis virus G glycoprotein (VSV-G) and a nucleic acid binding protein selected from the group consisting of histones, SSBP-1 and RNaseIII, and at least one nucleic acid; and
   administering to said subject a pharmaceutically active amount of said therapeutic compound.

\* \* \* \* \*